United States Patent
Watson et al.

(10) Patent No.: US 10,124,040 B2
(45) Date of Patent: Nov. 13, 2018

(54) METHOD FOR PREPARING CRYSTALLINE INSULIN OR INSULIN ANALOG COMPOSITIONS

(71) Applicants: Merck Sharp & Dohme Corp., Rahway, NJ (US); Douglas S. Watson, Elkton, VA (US); Allison C. Ortigosa, Elkton, VA (US); Mark C. Sleevi, Longmont, CO (US); Kathryn M. Story, Elkton, VA (US)

(72) Inventors: Douglas S. Watson, Harrisonburg, VA (US); Allison C. Ortigosa, Harrisonburg, VA (US); Mark C. Sleevi, Longmont, CO (US); Kathryn M. Story, Harrisonburg, VA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/505,124

(22) PCT Filed: Aug. 21, 2015

(86) PCT No.: PCT/US2015/046199
§ 371 (c)(1),
(2) Date: Feb. 20, 2017

(87) PCT Pub. No.: WO2016/032869
PCT Pub. Date: Mar. 3, 2016

(65) Prior Publication Data
US 2017/0209545 A1    Jul. 27, 2017

Related U.S. Application Data

(60) Provisional application No. 62/041,743, filed on Aug. 26, 2014.

(51) Int. Cl.
*A61K 38/28* (2006.01)
*A61K 47/02* (2006.01)
(Continued)

(52) U.S. Cl.
CPC .............. *A61K 38/28* (2013.01); *A61K 9/143* (2013.01); *A61K 9/145* (2013.01); *A61K 47/02* (2013.01); *A61K 47/10* (2013.01); *C07K 14/62* (2013.01)

(58) Field of Classification Search
CPC .................................................... A61K 38/28
See application file for complete search history.

(56) References Cited

U.S. PATENT DOCUMENTS

| | | | |
|---|---|---|---|
| 2,920,014 | A | 1/1960 | Petersen et al. |
| 3,719,655 | A | 3/1973 | Jackson |

(Continued)

FOREIGN PATENT DOCUMENTS

| | | |
|---|---|---|
| CA | 2151563 | 8/2007 |
| DE | 69829953 | 3/2006 |

(Continued)

OTHER PUBLICATIONS

Bakaysa, et al., Physicochemical Basis for the Rapid time-action of Lys B28 Pro B29-insulin: Dissociation of a protein-ligand complex; Protein Science 1996, vol. 5, pp. 2521-2531.

(Continued)

*Primary Examiner* — Benjamin J Packard
(74) *Attorney, Agent, or Firm* — John David Reilly; Laura M. Ginkel

(57) ABSTRACT

A method for crystallizing insulin or insulin analogs under alkaline conditions in the presence of zinc, purifying the crystals by filtering through a filter, and drying the crystals (Continued)

captured on the filter to produce crystalline insulin or insulin analog compositions is described. Method has been exemplified with insulin lispro.

17 Claims, 6 Drawing Sheets

(51) Int. Cl.
  *A61K 47/10* (2017.01)
  *A61K 9/14* (2006.01)
  *C07K 14/62* (2006.01)

(56) References Cited

U.S. PATENT DOCUMENTS

| | | | |
|---|---|---|---|
| 5,028,587 | A | 7/1991 | Dorschug et al. |
| 5,474,978 | A | 12/1995 | Bakaysa et al. |
| 5,504,188 | A | 4/1996 | Baker et al. |
| 5,597,893 | A | 1/1997 | Baker et al. |
| 5,952,297 | A | 9/1999 | De Felippis et al. |
| 7,193,035 | B2 | 3/2007 | Berchtold |
| 2005/0054818 | A1 | 3/2005 | Brader et al. |
| 2014/0155574 | A1 | 6/2014 | Wang et al. |

FOREIGN PATENT DOCUMENTS

| | | | | |
|---|---|---|---|---|
| EP | 2708550 | | 3/2014 | |
| WO | 199834953 | | 8/1998 | |
| WO | WO 2012152175 | A1 * | 11/2012 | ............. C07K 14/62 |

OTHER PUBLICATIONS

Birnbaum et al., Assembly & Dissociation of Human Insulin and Lys B28 Pro B29-insulin Hexamers: A Comparison Study; Pharmaceutical Research 1997, vol. 14, pp. 25-36.

Brange & Langkjoer, in Stability and characterization of protein and peptide drugs: Case histories, Wang, Y. J.; Pearlman, R., Eds. 1993; pp. 315-350.

Brange et al., Chemical Stability of Insulin 3. Influence of excipients, formulation, and pH; Acta Pharmaceutica Nordica 1992, vol. 4, pp. 149-158.

Brange et al., Neutral Insulin Solutions Physically Stabilized by Addition of Zn; Diabetic Medicine 1986, vol. 3, pp. 532-536.

Brange et al., Chemical Stability of Insulin. 1. Hydrolytic Degradation During Storage of Pharmaceutical Preparations; Pharmaceutical Research 1992, vol. 9, pp. 715-726.

Brems et al., Improved Insulin Stability Through Amino Acid Substitution; Protein Engineering Design & Selection 1992, vol. 5, pp. 519-525.

Chawdhury et al., The Crystal Instructions of Three non-pancreatic human insulins; Diabetologia 1983, vol. 25, pp. 460-464.

Ciszak et al., Role of C-terminal B-chain Residues in Insulin Assembly: the Structure of Hexameric Lys B28 Pro B29 human insulin; Structure 1995, vol. 3, pp. 615-622.

Derewenda et al., Phenol Stabilizes more Helix in a New Symmetrical Zinc Insulin Hexamer; Nature 1989, vol. 338, pp. 594-596.

Hallas-Moller et al., Crystalline and Amorphous Insulin-zinc Compounds with Prolonged Action; Science 1952, vol. 116, pp. 394-398.

Kang et al., Subcutaneous Insulin Absorption Explained by Insulin's Physicochemical Properties; Diabetes Care 1991, vol. 14, pp. 942-948.

Smith et al., Structural Stability in the 4-zinc human insulin hexamer; Proceedings of the National Academy of Sciences 1984, vol. 81, pp. 7093-7097.

Walsh, Therapeutic insulins and their large-scale manufacture; Applied Microbiology and Biotechnology 2005, vol. 67, pp. 151-159.

\* cited by examiner

METHOD FOR PREPARING CRYSTALLINE INSULIN OR INSULIN ANALOG COMPOSITIONS

CROSS REFERENCE TO RELATED APPLICATIONS

This application is the § 371 National Stage of International Application No. PCT/US2015/046199 filed on Aug. 21, 2015, which claims the benefit under 35 U.S.C. 119(e) of U.S. Provisional Application No. 62/041,743, filed Aug. 26, 2014.

BACKGROUND OF THE INVENTION (1) Field of the Invention

The present invention relates to a method for crystallizing insulin or insulin analogs under alkaline conditions in the presence of zinc, purifying the crystals by filtering through a filter, and drying the crystals captured on the filter to produce crystalline insulin or insulin analog compositions.

(2) Description of Related Art

Diabetes mellitus is a chronic metabolic disorder caused by either a deficiency of insulin generated by pancreatic beta cells (Type 1) or an acquired cellular resistance to insulin (Type 2). Both Type 1 and Type 2 diabetes result in hyperglycemia, which can in turn result in long term complications. Since the introduction of insulin in 1921, all forms of diabetes have become treatable.

It is well known in the art that insulin may be crystallized in the presence of zinc ions, resulting in a crystalline preparation with significant benefits over amorphous, uncrystallized insulin with regards to stability, storage, formulation, and/or administration. Methods for crystallizing insulin lispro have been disclosed in U.S. Pat. Nos. 5,952, 297; 5,028,587; 5,504,188; 5,597,893; 5,952,297 and 7,193, 035. Methods for crystallizing an insulin analog in the absence of zinc ions is disclosed in U.S. Pat. No. 7,193,035, which discloses zinc-free crystallization of an insulin analog performed at a pH in the range of about 4.0 to about 7.5. Methods for crystallizing mixed crystals of insulin and insulin derivatives is disclosed in U.S. Pat. No. 5,028,587.

In the presence of zinc, human insulin self-assembles into stable hexameric structures (Chawdhury et al., Diabetologia 1983, 25, 460-464; Smith et al., Proceedings of the National Academy of Sciences 1984, 81, 7093-7097). Upon injection, the dissociation of human insulin hexamers into dimers and monomers is the rate-limiting step in absorption, causing a 30-45 minute delay in onset of action after administration (Kang et al., Diabetes Care 1991, 14, 942-948). In insulin lispro, the reversal of lysine and proline at positions 28 and 29 of the B-chain destabilize insulin dimer interactions (Ciszak et al., Structure 1995, 3, 615-622). When stabilized by a phenolic additive, hexameric insulin lispro preparations exhibit comparable stability to human insulin (Derewenda et al., Nature 1989, 338, 594-596; Bakaysa, D. L.; Radziuk, J.; Havel, H. A.; Brader et al., Protein Science 1996, 5, 2521-2531). However, after injection and dissipation of the phenolic preservative, hexameric insulin lispro dissociates into monomers more quickly than human insulin, resulting in a more rapid onset of action (Birnbaum et al., Pharmaceutical Research 1997, 14, 25-36).

Zinc content plays an important role in chemical and physical stability of pharmaceutical insulin formulations (Brange & Langkjoer, In Stability and characterization of protein and peptide drugs: Case histories, Wang, Y. J.; Pearlman, R., Eds. 1993; pp 315-350). Relative to monomeric insulin, hexameric preparations have greatly reduced susceptibility to chemical degradation, including deamidation (Brange et al., Pharmaceutical Research 1992, 9, 715-726) and covalent aggregation (Brange et al., Acta Pharmaceutica Nordica 1992, 4, 149-158). Physical stabilization of the hexamer structure by zinc also reduces the propensity for fibrillation (Brange et al., Diabetic Medicine 1986, 3, 532-536), while excess zinc causes insulin to precipitate into a crystalline suspension (Hallas-Moller et al., Science 1952, 116, 394-398). Zinc content therefore impacts the shelf life, biological activity, immunogenicity potential, and physical form of insulin formulations (Brange & Langkjoer, Op. cit.). For pharmaceutical insulin lispro solutions, a precise ratio of 3 zinc atoms per insulin hexamer was determined to be optimal (U.S. Pat. No. 5,474,978).

Commercial insulin manufacturing processes typically include a crystallization step to convert purified insulin into solid form, providing increased stability for bulk storage prior to formulation and filling (Walsh, Applied Microbiology and Biotechnology 2005, 67, 151-159). Classical insulin crystallization processes involve preparation of an acidic solution containing organic acid (acetic or citric), approximately 2 g/L insulin, and zinc. The solution pH is then adjusted to near the isoelectric point of insulin (pH 5.5-6.0), which initiates crystal formation (U.S. Pat. No. 2,920,014) During development of insulin lispro, it was noted that these conditions did not result in crystal formation, likely due to the reduced propensity of insulin lispro to self-associate (Brems et al., Protein Engineering Design & Selection 1992, 5, 519-525.). When this process was modified to include a phenolic stabilizer (phenol or resorcinol, but not m-cresol) at approximately 0.2%, insulin lispro crystals were obtained (U.S. Pat. No. 5,504,188,). A zinc-free insulin lispro crystallization process was also developed based on the classical "pH 8.2 process", in which crystalline insulin salts are obtained from insulin solutions containing alkali metal cations or ammonium cations at alkaline pH (optimally pH 8.2) (U.S. Pat. No. 3,719,655). To adapt the process for successful crystallization of insulin lispro, a phenolic stabilizer was added and the optimal pH adjusted to 9.0 (U.S. Pat. No. 5,597,893). Though successful, these crystallization processes featured somewhat restrictive design spaces and were not robust with respect to the choice of phenolic stabilizer used.

While there are methods available for crystallizing insulin and insulin analogs, there is a need in the art for alternative methods of crystallizing insulin and insulin analogs such as insulin lispro.

BRIEF SUMMARY OF THE INVENTION

The present invention provides an alternative insulin lispro crystallization process. Motivated by the criticality of zinc content in the stability of insulin lispro, we sought to develop a robust process in which crystallization parameters could be modulated to assure control the zinc level in the resulting crystalline product. We discovered that insulin lispro could be crystallized in the presence of zinc at alkaline pH, under conditions distinct from those reported previously. Using this process, the levels of organic acid, base, and zinc could be varied to influence the zinc content of the dried drug substance. Moreover, cake wash conditions were developed that provided additional control of zinc content. This novel crystallization process may have broad utility for the commercial manufacture of insulin lispro and other insulin analogs.

In general, the present invention provides a method for crystallizing insulin and insulin analogs such as insulin lispro under alkaline conditions in the presence of zinc. In an effort to provide improved methods for preparing crystalline insulin lispro, we have found that insulin and insulin analogs such as insulin lispro may be crystallized at a pH that is about 1.5 to about 3.0 units above the pI of the insulin (e.g., a pH from about 7.0 to 8.5) in the presence of zinc. The present invention has been exemplified with insulin lispro. Current methods for preparing insulin lispro crystals include crystallizing the insulin lispro at an alkaline pH from about 8.5 to about 9.5 in the absence of zinc or at an acidic pH of about 5.5 to about 6.5 in the presence of zinc. The present invention enables the production of large, ordered crystals of the insulin lispro that may be about 10 µm or greater in size and which are amenable to purifying by collecting the crystals in a filter apparatus and drying the crystals in the same filtering apparatus to produce crystalline insulin compositions.

Therefore, the present invention provides a method for preparing insulin or insulin analog crystals which comprises crystallizing the insulin or insulin analog from an aqueous solution comprising the insulin or insulin analog, a water miscible organic solvent, a crystal stabilizing agent, which may optionally include a trace amount of phenol, zinc salt, wherein the solution has a pH greater than the pI of the insulin or insulin analog.

In particular aspects, the insulin or insulin analog may be crystallized at a pH that is at least 1.0 or more pH units greater than the isoelectric point (pI) of the insulin or insulin analog. In particular aspects, the insulin lispro may be crystallized at a pH that is at least 1.5 or more pH units greater than the isoelectric point (pI) of the insulin or insulin analog. In particular aspects, the insulin or insulin analog may be crystallized at a pH that is at least 2.0 or more pH units greater than the isoelectric point (pI) of the insulin or insulin analog. In particular aspects, the insulin or insulin analog may be crystallized at a pH that is at least 2.5 or more pH units greater than the isoelectric point (pI) of the insulin or insulin analog. In particular aspects, the insulin or insulin analog may be crystallized at a pH that is about 1.0 and 3.0 pH units greater than the isoelectric point (pI) of the insulin or insulin analog. In particular aspects, the insulin or insulin analog may be crystallized at a pH that is between about 1.5 and 3.0 pH units greater than the isoelectric point (pI) of the insulin or insulin analog. In particular aspects, the insulin or insulin analog may be crystallized at a pH that is between about 2.0 and 3.0 pH units greater than the isoelectric point (pI) of the insulin or insulin analog. In particular aspects, the method may be performed at a temperature at room temperature or within the range of about 17° C. to 23° C., or about 20° C., and at a pH within the range of about 7.0 to 8.5 pH units or about 7.7 pH units. In further aspects, the solution is incubated with agitation or stirring. The agitation may be provided by a low shear impeller, for example, an axial flow impeller such as marine impeller or pitched-blade impeller.

In a further aspect of the method, the solution comprises ammonium acetate, which may in particular aspects comprise ammonium acetate at a concentration of about 750 mM to 850 mM. In further embodiments, the ammonium acetate concentration is about 800 mM.

In a further aspect of the method, the concentration of the insulin or insulin analog in the solution may be about 1 to about 5 grams of insulin or insulin analog per liter of solution. In a further aspect of the method, the concentration of the insulin lispro in the solution may be about 1.5 to about 2.5 grams of insulin or insulin analog per liter of solution. In a further aspect, the concentration of the insulin or insulin analog in the solution may be about 2.2 grams of insulin or insulin analog per liter of solution.

In a further aspect of the method, the solution may comprise from about 0% (v/v) to about 20% (v/v) of the water miscible organic solvent. In a further aspect of the method, the solution comprises from about 2.5% (v/v) to about 9.0% (v/v) of the water miscible organic co-solvent. In a further aspect of the method, the solution comprises from about 1% (v/v) to about 5% (v/v) of the water miscible organic co-solvent. In a further aspect, the solution comprises about 3.6% (v/v) of the water miscible organic solvent. In particular aspects, the water miscible organic solvent is isopropanol.

In particular aspects, the solution comprises from about 5 to 10 mM or 6.8 to 7.2 mM of the crystal stabilizing agent and optionally a trace amount of the phenol, e.g., about 0.02 to 0.08 mM or about 0.05 to 0.0.7 mM phenol. In particular aspects, the solution comprises about 7.0 mM of the crystal stabilizing agent. In particular aspects, the solution comprises about 0.060 mM of the phenol. In a further aspect of the method, the crystal stabilizing agent is a phenolic agent selected from the group comprising resorcinol, cresol, meta-cresol, methyl p-hydroxybenzoate, and methyl 4-hydroxybenzoate. In a particular aspect, the crystal stabilizing agent is meta-cresol. In particular aspects, the crystal stabilizing agent is meta-cresol and the solution further includes phenol at a concentration not more than 0.08 mM. In particular aspects, the solution includes the crystal stabilizing agent and does not include phenol.

In a further aspect of the method, the amount of zinc salt in the solution is an amount sufficient to provide at least two atoms of zinc per six molecules of insulin or insulin analog. In particular aspects, the amount of zinc salt in the solution is an amount sufficient to provide two or three atoms of zinc per six molecules of insulin or insulin analog. In particular aspects, the amount of zinc salt in the solution is an amount sufficient to provide two to three atoms of zinc per six molecules of insulin or insulin analog. In particular aspects, the amount of zinc salt in the solution is an amount sufficient to provide at least two and no more than three atoms of zinc per six molecules of insulin or insulin analog. In particular aspects, the amount of zinc salt in the solution is an amount sufficient so that the insulin or insulin analog crystals comprise at least two and no more than three atoms of zinc per six molecules of insulin or insulin analog. In particular aspects, the amount of zinc salt in the solution is an amount sufficient so that the insulin or insulin analog crystals comprise two to three atoms of zinc per six molecules of insulin or insulin analog. In particular aspects, the amount of zinc salt in the solution is an amount sufficient so that the insulin or insulin analog crystals comprise two and a half atoms of zinc per six molecules of insulin or insulin analog.

In particular aspects, following the crystallization of the insulin or insulin analog, a crystal slurry comprising the insulin or insulin analog crystals is produced by allowing the insulin lispro crystals in the solution to settle in the solution and the solution decanted from the settled insulin or insulin analog crystals to produce a decanted crystal slurry. In particular aspects, the insulin or insulin analog crystals are allowed to settle for about five hours or more prior to decanting the solution to produce the decanted crystal slurry.

In a further aspect, the decanted crystal slurry is applied to a filter apparatus to remove remaining solution from the decanted crystal slurry to produce a crystal cake bed and drying the crystal cake bed to provide the insulin or insulin analog crystals.

In a further aspect, the decanted crystal slurry is applied to a filter apparatus to remove remaining solution from the decanted crystal slurry to produce a crystal cake bed, washing the crystal cake bed with a cake wash solution, and drying the crystal cake bed to provide the insulin or insulin analog crystals.

In particular aspects, the cake wash solution comprises a water miscible organic solvent, a crystal stabilizing agent, and a zinc salt wherein the solution has a pH that is about 4.5 to 8.5.

In particular aspects, the filter apparatus is a Nutsche filter.

The present invention further provides a method for preparing insulin or insulin analog crystals comprising (a) providing a solution comprising the insulin or insulin analog, a water miscible organic solvent, and a crystal stabilizing agent, wherein the solution has a pH that is about 7.0 to 8.5; and (b) adding a zinc salt to the solution to provide a crystallizing solution and incubating the crystallizing solution for a time sufficient for the insulin or insulin analog to crystallize produce the insulin or insulin analog crystals.

In particular aspects, following the crystallization of the insulin or insulin analog, a crystal slurry comprising the insulin or insulin analog crystals is produced by allowing the insulin or insulin analog crystals in the crystallizing solution to settle in the crystallizing solution and the crystallizing solution decanted from the settled insulin or insulin analog crystals to produce a decanted crystal slurry. The insulin or insulin analog crystals may be allowed to settle for about five hours or more prior to decanting the crystallizing solution to produce the decanted crystal slurry.

In particular aspects, the decanted crystal slurry is applied to a filter apparatus to remove remaining crystallizing solution from the decanted crystal slurry to produce a crystal cake bed and drying the crystal cake bed to provide the crystal insulin or insulin analog.

In particular aspects, the decanted crystal slurry is applied to a filter apparatus to remove remaining crystallizing solution from the decanted crystal slurry to produce a crystal cake bed, washing the crystal cake bed with a cake wash solution, and drying the crystal cake bed to provide the crystal insulin or insulin analog.

In particular aspects, the insulin or insulin analog may be crystallized at a pH that is at least 1.0 or more pH units greater than the isoelectric point (pI) of the insulin or insulin analog. In particular aspects, the insulin or insulin analog may be crystallized at a pH that is at least 1.5 or more pH units greater than the isoelectric point (pI) of the insulin or insulin analog. In particular aspects, the insulin or insulin analog may be crystallized at a pH that is at least 2.0 or more pH units greater than the isoelectric point (pI) of the insulin or insulin analog. In particular aspects, the insulin or insulin analog may be crystallized at a pH that is at least 2.5 or more pH units greater than the isoelectric point (pI) of the insulin or insulin analog. In particular aspects, the insulin or insulin analog may be crystallized at a pH that is about 1.0 and 3.0 pH units greater than the isoelectric point (pI) of the insulin or insulin analog. In particular aspects, the insulin or insulin analog may be crystallized at a pH that is between about 1.5 and 3.0 pH units greater than the isoelectric point (pI) of the insulin or insulin analog. In particular aspects, the insulin or insulin analog may be crystallized at a pH that is between about 2.0 and 3.0 pH units greater than the isoelectric point (pI) of the insulin or insulin analog. In particular aspects, the method may be performed at a temperature at room temperature or within the range of about 17° C. to 23° C., or about 20° C., and at a pH within the range of about 7.0 to 8.5 pH units or about 7.7 pH units. In further aspects, the solution is incubated with agitation or stirring. The agitation may be provided by a low shear impeller, for example, an axial flow impeller such as marine impeller or pitched-blade impeller.

In a further aspect of the method, the solution comprises ammonium acetate, which may in particular aspects comprise ammonium acetate at a concentration of about 750 mM to 850 mM. In further embodiments, the ammonium acetate concentration is about 800 mM.

In a further aspect of the method, the concentration of the insulin or insulin analog in the solution may be about 1 to about 5 grams of insulin or insulin analog per liter of solution. In a further aspect of the method, the concentration of the insulin or insulin analog in the solution may be about 1.5 to about 2.5 grams of insulin or insulin analog per liter of solution. In a further aspect, the concentration of the insulin or insulin analog in the solution may be about 2.2 grams of insulin or insulin analog per liter of solution.

In a further aspect of the method, the solution may comprise from about 0% (v/v) to about 20% (v/v) of the water miscible organic solvent. In a further aspect of the method, the solution comprises from about 2.5% (v/v) to about 9.0% (v/v) of the water miscible organic co-solvent. In a further aspect of the method, the solution comprises from about 1% (v/v) to about 5% (v/v) of the water miscible organic co-solvent. In a further aspect, the solution comprises about 3.6% (v/v) of the water miscible organic solvent. In particular aspects, the water miscible organic solvent is isopropanol.

In particular aspects, the solution comprises from about 5 to 10 mM or 6.8 to 7.2 mM of the crystal stabilizing agent and optionally a trace amount of the phenol, e.g., about 0.02 to 0.08 mM or about 0.05 to 0.07 mM phenol. In particular aspects, the solution comprises about 7.0 mM of the crystal stabilizing agent. In particular aspects, the solution comprises about 0.060 mM of the phenol. In a further aspect of the method, the crystal stabilizing agent is a phenolic agent selected from the group comprising resorcinol, cresol, meta-cresol, methyl p-hydroxybenzoate, and methyl 4-hydroxybenzoate. In a particular aspect, the crystal stabilizing agent is meta-cresol. In particular aspects, the crystal stabilizing agent is meta-cresol and the solution further includes phenol at a concentration not more than 0.08 mM. In particular aspects, the solution includes the crystal stabilizing agent and does not include phenol.

In a further aspect of the method, the amount of zinc salt in the solution is an amount sufficient to provide at least two atoms of zinc per six molecules of insulin or insulin analog. In particular aspects, the amount of zinc salt in the solution is an amount sufficient to provide two or three atoms of zinc per six molecules of insulin or insulin analog. In particular aspects, the amount of zinc salt in the solution is an amount sufficient to provide two to three atoms of zinc per six molecules of insulin or insulin analog. In particular aspects, the amount of zinc salt in the solution is an amount sufficient to provide at least two and no more than three atoms of zinc per six molecules of insulin or insulin analog. In particular aspects, the amount of zinc salt in the solution is an amount sufficient so that the insulin or insulin analog crystals comprise at least two and no more than three atoms of zinc per six molecules of insulin or insulin analog. In particular aspects, the amount of zinc salt in the solution is an amount sufficient so that the insulin or insulin analog crystals comprise two to three atoms of zinc per six molecules of insulin or insulin analog. In particular aspects, the amount of zinc salt in the solution is an amount sufficient so that the insulin or insulin analog crystals comprise two and a half atoms of zinc per six molecules of insulin or insulin analog.

In particular aspects, the cake wash solution comprises a water miscible organic solvent, a crystal stabilizing agent, and a zinc salt wherein the cake wash solution has a pH that is about 4.5 to 8.5. In a further aspect, the pH of the cake wash solution is about 5.5.

In particular aspects, the cake wash solution further includes from about 0% (v/v) to about 10% (v/v) of the water miscible organic solvent. In a further aspect of the method, the cake wash solution comprises about 5.0% (v/v) of the water miscible organic solvent. In particular aspects, the water miscible organic solvent is isopropanol.

In particular aspects, the cake wash solution comprises ammonium acetate, which may in particular aspects comprise ammonium acetate at a concentration of about 200 mM to 800 mM. In further embodiments, the ammonium acetate concentration is about 400 mM.

In particular aspects, the cake wash solution comprises from about 5 to 10 mM of the crystal stabilizing agent. In particular aspects, the solution comprises about 7.0 mM of the crystal stabilizing agent. In a further aspect of the method, the crystal stabilizing agent is a phenolic agent selected from the group comprising resorcinol, cresol, meta-cresol, methyl p-hydroxybenzoate, and methyl 4-hydroxybenzoate. In a particular aspect, the crystal stabilizing agent is meta-cresol.

In particular aspects, the cake wash solution comprises about 400 mM acetate, about 5.0% (v/v) isopropanol, about 7 mM m-cresol, about 0.4 mM zinc chloride, at a pH of about 5.5.

The present invention further provides a method for producing insulin or insulin analog crystals with two to three zinc atoms per hexamer of insulin or insulin analog comprising (a) providing a decanted crystal slurry comprising insulin or insulin analog crystals, a water miscible organic solvent, a crystal stabilizing agent, and a zinc salt wherein the crystal slurry has a pH that is about 7.0 to 8.5; (b) adding a cake wash solution to the decanted crystal slurry to provide a mixture and incubating the mixture for a time sufficient to remove unbound zinc from the insulin or insulin analog crystals, and (c) removing the cake wash solution from the mixture to provide the insulin or insulin analog crystals with two to three zinc atoms per hexamer of insulin or insulin analog.

In particular aspects, the decanted crystal slurry is applied to a filter apparatus prior to adding the cake wash solution. In particular aspects, the decanted crystal slurry is applied to a filter apparatus prior and formed into a crystal cake prior to adding the cake wash solution.

In particular aspects, the decanted crystal slurry has a zinc content greater than two to three zinc molecules per hexamer of insulin or insulin analog. In particular aspects, after removing the cake wash solution the zinc content of the insulin or insulin analog crystals is two zinc molecules per hexamer.

In particular aspects, after removing the cake wash solution the zinc content of the insulin or insulin analog crystals is two to three zinc molecules per hexamer.

In particular aspects, the cake wash solution comprises a water miscible organic solvent, a crystal stabilizing agent, and zinc salt, wherein the solution has a pH that is about 4.5 to 8.5. In a further aspect, the pH of the cake wash solution is about 5.5.

In particular aspects, the water miscible organic solvent is selected from the group consisting of ethanol, methanol, acetone, and isopropanol. In particular aspects, the water miscible organic solvent is isopropanol. In particular aspects, the water miscible organic solvent is present in the decanted slurry in an amount which corresponds to about 2.5% (v/v) to 9.0% (v/v) of the solution. In particular aspects, the cake wash solution further includes from about 0% (v/v) to about 10% (v/v) of the water miscible organic solvent. In a further aspect of the method, the cake wash solution comprises about 5.0% (v/v) of the water miscible organic solvent.

In particular aspects, the cake wash solution comprises ammonium acetate, which may in particular aspects comprise ammonium acetate at a concentration of about 200 mM to 800 mM. In further embodiments, the ammonium acetate concentration is about 400 mM.

In particular aspects, the cake wash solution comprises about 400 mM acetate, about 5.0% (v/v) isopropanol, about 7 mM m-cresol, about 0.4 mM zinc chloride, at a pH of about 5.5.

In particular aspects, the crystal stabilizing agent is resorcinol, cresol, meta-cresol, methyl p-hydroxybenzoate, or methyl 4-hydroxybenzoate. In particular aspects, the crystal stabilizing agent is meta-cresol. In particular aspects, the decanted slurry comprises about 5 to mM or about 7.0 mM of the crystal stabilizing agent. In particular aspects, the cake wash solution comprises from about 5 to 10 mM of the crystal stabilizing agent. In particular aspects, the cake wash solution comprises about 7.0 mM of the crystal stabilizing agent.

In particular aspects, the zinc salt is zinc chloride.

In particular aspects, the insulin or insulin analog crystals in step (c) are dried to provide the insulin or insulin analog crystals with two to three zinc atoms per hexamer of insulin or insulin analog.

The present invention further provides a method for preparing insulin or insulin analog crystals with two to three zinc atoms per hexamer of insulin or insulin analog, comprising (a) providing a solution comprising the insulin or insulin analog, a water miscible organic solvent, and a crystal stabilizing agent, wherein the solution has a pH that is about 7.0 to 8.5; (b) adding a zinc salt to the solution to provide a crystallizing solution and incubating the crystallizing solution for a time sufficient produce insulin or insulin analog crystals; (c) allowing the insulin or insulin analog crystals in the solution to settle in the crystallizing solution and decanting the crystallizing solution from the settled insulin or insulin analog crystals to produce a decanted crystal slurry; (d) applying the decanted crystal slurry to a filter apparatus to remove remaining crystallizing solution from the decanted crystal slurry to produce a crystal cake bed; (e) adding a cake wash solution to the decanted crystal slurry to provide a mixture and incubating the mixture for a time sufficient to remove unbound zinc from the insulin or insulin analog crystals, and (f) removing the cake wash solution from the mixture to provide the insulin or insulin analog crystals with two to three zinc atoms per hexamer of insulin or insulin analog.

In particular aspects, the decanted crystal slurry has a zinc content greater than two to three zinc molecules per hexamer of insulin or insulin analog. In particular aspects, after removing the cake wash solution the zinc content of the insulin or insulin analog crystals is two zinc molecules per hexamer.

In particular aspects, after removing the cake wash solution the zinc content of the insulin or insulin analog crystals is three zinc molecules per hexamer.

In particular aspects, the cake wash solution comprises a water miscible organic solvent, a crystal stabilizing agent, and zinc salt, wherein the solution has a pH that is about 4.5 to 8.5. In a further aspect, the pH of the cake wash solution is about 5.5.

In particular aspects, the water miscible organic solvent is selected from the group consisting of ethanol, methanol, acetone, and isopropanol. In particular aspects, the water miscible organic solvent is isopropanol. In particular aspects, the water miscible organic solvent is present in the solution in an amount which corresponds to about 2.5% (v/v) to 9.0% (v/v) of the solution. In particular aspects, the cake wash solution further includes from about 0% (v/v) to about 10% (v/v) of the water miscible organic solvent. In a further aspect of the method, the cake wash solution comprises about 5.0% (v/v) of the water miscible organic solvent.

In particular aspects, the solution comprises ammonium acetate, which may in particular aspects comprise ammonium acetate at a concentration of about 750 mM to 850 mM. In further embodiments, the ammonium acetate concentration is about 800 mM.

In particular aspects, the cake wash solution comprises ammonium acetate, which may in particular aspects comprise ammonium acetate at a concentration of about 200 mM to 800 mM. In further embodiments, the ammonium acetate concentration is about 400 mM.

In particular aspects, the cake wash solution comprises about 400 mM acetate, about 5.0% (v/v) isopropanol, about 7 mM m-cresol, about 0.4 mM zinc chloride, at a pH of about 5.5.

In particular aspects, the crystal stabilizing agent is resorcinol, cresol, meta-cresol, methyl p-hydroxybenzoate, or methyl 4-hydroxybenzoate. In particular aspects, the crystal stabilizing agent is meta-cresol. In particular aspects, the decanted slurry comprises about 5 to mM or about 7.0 mM of the crystal stabilizing agent. In particular aspects, the cake wash solution comprises from about 5 to 10 mM of the crystal stabilizing agent. In particular aspects, the cake wash solution comprises about 7.0 mM of the crystal stabilizing agent. In particular aspects, the solution and the cake wash solution comprise the crystal stabilizing agent and excludes phenol. However, in particular aspects, the solution may include a trace amount of phenol.

In particular aspects, the zinc salt is zinc chloride.

In particular aspects, the insulin or insulin analog crystals in step (f) are dried to provide the insulin or insulin analog crystals with two to three zinc atoms per hexamer of insulin or insulin analog.

The present invention further provides a method for preparing insulin lispro crystals which comprises crystallizing the insulin lispro from an aqueous solution comprising the insulin lispro, a water miscible organic solvent, a crystal stabilizing agent, optionally a trace amount of phenol, zinc salt, wherein the solution has a pH greater than the pI of the insulin lispro.

In particular aspects, the insulin lispro may be crystallized at a pH that is at least 1.0 or more pH units greater than the isoelectric point (pI) of the insulin lispro. In particular aspects, the insulin lispro may be crystallized at a pH that is at least 1.5 or more pH units greater than the isoelectric point (pI) of the insulin lispro. In particular aspects, the insulin lispro may be crystallized at a pH that is at least 2.0 or more pH units greater than the isoelectric point (pI) of the insulin lispro. In particular aspects, the insulin lispro may be crystallized at a pH that is at least 2.5 or more pH units greater than the isoelectric point (pI) of the insulin lispro. In particular aspects, the insulin lispro may be crystallized at a pH that is about 1.0 and 3.0 pH units greater than the isoelectric point (pI) of the insulin lispro. In particular aspects, the insulin lispro may be crystallized at a pH that is between about 1.5 and 3.0 pH units greater than the isoelectric point (pI) of the insulin lispro. In particular aspects, the insulin lispro may be crystallized at a pH that is between about 2.0 and 3.0 pH units greater than the isoelectric point (pI) of the insulin lispro. In particular aspects, the method may be performed at a temperature at room temperature or within the range of about 17° C. to 23° C., or about 20° C., and at a pH within the range of about 7.0 to 8.5 pH units or about 7.7 pH units. In further aspects, the solution is incubated with agitation or stirring. The agitation may be provided by a low shear impeller, for example, an axial flow impeller such as marine impeller or pitched-blade impeller.

In a further aspect of the method, the solution comprises ammonium acetate, which may in particular aspects comprise ammonium acetate at a concentration of about 750 mM to 850 mM. In further embodiments, the ammonium acetate concentration is about 800 mM.

In a further aspect of the method, the concentration of the insulin lispro in the solution may be about 1 to about 5 grams of insulin lispro per liter of solution. In a further aspect of the method, the concentration of the insulin lispro in the solution may be about 1.5 to about 2.5 grams of insulin lispro per liter of solution. In a further aspect, the concentration of the insulin lispro in the solution may be about 2.2 grams of insulin lispro per liter of solution.

In a further aspect of the method, the solution may comprise from about 0% (v/v) to about 20% (v/v) of the water miscible organic solvent. In a further aspect of the method, the solution comprises from about 2.5% (v/v) to about 9.0% (v/v) of the water miscible organic co-solvent. In a further aspect of the method, the solution comprises from about 1% (v/v) to about 5% (v/v) of the water miscible organic co-solvent. In a further aspect, the solution comprises about 3.6% (v/v) of the water miscible organic solvent. In particular aspects, the water miscible organic solvent is isopropanol.

In particular aspects, the solution comprises from about 5 to 10 mM or 6.8 to 7.2 mM of the crystal stabilizing agent and optionally a trace amount of the phenol, e.g., about 0.02 to 0.08 mM or about 0.05 to 0.0.7 mM phenol. In particular aspects, the solution comprises about 7.0 mM of the crystal stabilizing agent. In particular aspects, the solution comprises about 0.060 mM of the phenol. In a further aspect of the method, the crystal stabilizing agent is a phenolic agent selected from the group comprising resorcinol, cresol, meta-cresol, methyl p-hydroxybenzoate, and methyl 4-hydroxybenzoate. In a particular aspect, the crystal stabilizing agent is meta-cresol. In particular aspects, the crystal stabilizing agent is meta-cresol and the solution further includes phenol at a concentration not more than 0.08 mM. In particular aspects, the solution includes the crystal stabilizing agent and does not include phenol.

In a further aspect of the method, the amount of zinc salt in the solution is an amount sufficient to provide at least two atoms of zinc per six molecules of insulin lispro. In particular aspects, the amount of zinc salt in the solution is an amount sufficient to provide two or three atoms of zinc per six molecules of insulin lispro. In particular aspects, the amount of zinc salt in the solution is an amount sufficient to provide two to three atoms of zinc per six molecules of insulin or insulin analog. In particular aspects, the amount of zinc salt in the solution is an amount sufficient to provide at least two and no more than three atoms of zinc per six molecules of insulin lispro. In particular aspects, the amount of zinc salt in the solution is an amount sufficient so that the insulin lispro crystals comprises at least two and no more than three atoms of zinc per six molecules of insulin lispro. In particular aspects, the amount of zinc salt in the solution is an amount sufficient so that the insulin lispro crystals comprise two to three atoms of zinc per six molecules of insulin lispro.

In particular aspects, the cake wash solution comprises a water miscible organic solvent, a crystal stabilizing agent, and a zinc salt wherein the cake wash solution has a pH that is about 4.5 to 8.5. In a further aspect, the pH of the cake wash solution is about 5.5.

In particular aspects, the cake wash solution further includes from about 0% (v/v) to about 10% (v/v) of the water miscible organic solvent. In a further aspect of the method, the cake wash solution comprises about 5.0% (v/v) of the water miscible organic solvent. In particular aspects, the water miscible organic solvent is isopropanol.

In particular aspects, the cake wash solution comprises ammonium acetate, which may in particular aspects comprise ammonium acetate at a concentration of about 200 mM to 800 mM. In further embodiments, the ammonium acetate concentration is about 400 mM.

In particular aspects, the cake wash solution comprises from about 5 to 10 mM of the crystal stabilizing agent. In particular aspects, the solution comprises about 7.0 mM of the crystal stabilizing agent. In a further aspect of the method, the crystal stabilizing agent is a phenolic agent selected from the group comprising resorcinol, cresol, meta-cresol, methyl p-hydroxybenzoate, and methyl 4-hydroxybenzoate. In a particular aspect, the crystal stabilizing agent is meta-cresol.

In particular aspects, the cake wash solution comprises about 400 mM acetate, about 5.0% (v/v) isopropanol, about 7 mM m-cresol, about 0.4 mM zinc chloride, at a pH of about 5.5.

In particular aspects, following the crystallization of the insulin lispro, a crystal slurry comprising the insulin lispro crystals is produced by allowing the insulin lispro crystals in the solution to settle in the solution and the solution decanted from the settled insulin lispro crystals to produce a decanted crystal slurry. In particular aspects, the insulin lispro crystals are allowed to settle for about five hours or more prior to decanting the solution to produce the decanted crystal slurry.

In a further aspect, the decanted crystal slurry is applied to a filter apparatus to remove remaining solution from the decanted crystal slurry to produce a crystal cake bed and drying the crystal cake bed to provide the insulin lispro crystals.

In a further aspect, the decanted crystal slurry is applied to a filter apparatus to remove remaining solution from the decanted crystal slurry to produce a crystal cake bed, washing the crystal cake bed with a cake wash solution, and drying the crystal cake bed to provide the insulin lispro crystals.

In particular aspects, the cake wash solution comprises a water miscible organic solvent, a crystal stabilizing agent, and a zinc salt wherein the solution has a pH that is about 4.5 to 8.5.

The present invention further provides a method for preparing insulin lispro crystals comprising (a) providing a solution comprising the insulin lispro, a water miscible organic solvent, and a crystal stabilizing agent, wherein the solution has a pH that is about 7.0 to 8.5; and (b) adding a zinc salt to the solution to provide a crystallizing solution and incubating the crystallizing solution for a time sufficient for the insulin lispro to crystallize produce the insulin lispro crystals.

In particular aspects, following the crystallization of the insulin lispro, a crystal slurry comprising the insulin lispro crystals is produced by allowing the insulin lispro crystals in the crystallizing solution to settle in the crystallizing solution and the crystallizing solution decanted from the settled insulin lispro crystals to produce a decanted crystal slurry. The insulin lispro crystals may be allowed to settle for about five hours or more prior to decanting the crystallizing solution to produce the decanted crystal slurry.

In particular aspects, the decanted crystal slurry is applied to a filter apparatus to remove remaining crystallizing solution from the decanted crystal slurry to produce a crystal cake bed and drying the crystal cake bed to provide the crystal insulin lispro.

In particular aspects, the decanted crystal slurry is applied to a filter apparatus to remove remaining crystallizing solution from the decanted crystal slurry to produce a crystal cake bed, washing the crystal cake bed with a cake wash solution, and drying the crystal cake bed to provide the crystal insulin lispro.

In particular aspects, the insulin lispro may be crystallized at a pH that is at least 1.0 or more pH units greater than the isoelectric point (pI) of the insulin lispro. In particular aspects, the insulin lispro may be crystallized at a pH that is at least 1.5 or more pH units greater than the isoelectric point (pI) of the insulin lispro. In particular aspects, the insulin lispro may be crystallized at a pH that is at least 2.0 or more pH units greater than the isoelectric point (pI) of the insulin lispro. In particular aspects, the insulin lispro may be crystallized at a pH that is at least 2.5 or more pH units greater than the isoelectric point (pI) of the insulin lispro. In particular aspects, the insulin lispro may be crystallized at a pH that is about 1.0 and 3.0 pH units greater than the isoelectric point (pI) of the insulin lispro. In particular aspects, the insulin lispro may be crystallized at a pH that is between about 1.5 and 3.0 pH units greater than the isoelectric point (pI) of the insulin lispro. In particular aspects, the insulin lispro may be crystallized at a pH that is between about 2.0 and 3.0 pH units greater than the isoelectric point (pI) of the insulin lispro. In particular aspects, the method may be performed at a temperature at room temperature or within the range of about 17° C. to 23° C., or about 20° C., and at a pH within the range of about 7.0 to 8.5 pH units or about 7.7 pH units. In further aspects, the solution is incubated with agitation or stirring. The agitation may be provided by a low shear impeller, for example, an axial flow impeller such as marine impeller or pitched-blade impeller.

In a further aspect of the method, the solution comprises ammonium acetate, which may in particular aspects comprise ammonium acetate at a concentration of about 750 mM to 850 mM. In further embodiments, the ammonium acetate concentration is about 800 mM.

In a further aspect of the method, the concentration of the insulin lispro in the solution may be about 1 to about 5 grams of insulin lispro per liter of solution. In a further aspect of the method, the concentration of the insulin lispro in the solution may be about 1.5 to about 2.5 grams of insulin lispro per liter of solution. In a further aspect, the concentration of the insulin lispro in the solution may be about 2.2 grams of insulin lispro per liter of solution.

In a further aspect of the method, the solution may comprise from about 0% (v/v) to about 20% (v/v) of the water miscible organic solvent. In a further aspect of the method, the solution comprises from about 2.5% (v/v) to about 9.0% (v/v) of the water miscible organic co-solvent. In a further aspect of the method, the solution comprises from about 1% (v/v) to about 5% (v/v) of the water miscible organic co-solvent. In a further aspect, the solution comprises about 3.6% (v/v) of the water miscible organic solvent. In particular aspects, the water miscible organic solvent is isopropanol.

In particular aspects, the solution comprises from about 5 to 10 mM or 6.8 to 7.2 mM of the crystal stabilizing agent and optionally a trace amount of the phenol, e.g., about 0.02 to 0.08 mM or about 0.05 to 0.0.7 mM phenol. In particular aspects, the solution comprises about 7.0 mM of the crystal stabilizing agent. In particular aspects, the solution comprises about 0.060 mM of the phenol. In a further aspect of the method, the crystal stabilizing agent is a phenolic agent selected from the group comprising resorcinol, cresol, meta-cresol, methyl p-hydroxybenzoate, and methyl 4-hydroxybenzoate. In a particular aspect, the crystal stabilizing agent is meta-cresol. In particular aspects, the crystal stabilizing agent is meta-cresol and the solution further includes phenol at a concentration not more than 0.08 mM. In particular aspects, the solution includes the crystal stabilizing agent and does not include phenol.

In a further aspect of the method, the amount of zinc salt in the solution is an amount sufficient to provide at least two atoms of zinc per six molecules of insulin lispro. In particular aspects, the amount of zinc salt in the solution is an amount sufficient to provide two or three atoms of zinc per six molecules of insulin lispro. In particular aspects, the amount of zinc salt in the solution is an amount sufficient to provide two to three atoms of zinc per six molecules of insulin or insulin analog. In particular aspects, the amount of zinc salt in the solution is an amount sufficient to provide at least two and no more than three atoms of zinc per six molecules of insulin lispro. In particular aspects, the amount of zinc salt in the solution is an amount sufficient so that the insulin lispro crystals comprises at least two and no more than three atoms of zinc per six molecules of insulin lispro. In particular aspects, the amount of zinc salt in the solution is an amount sufficient so that the insulin lispro crystals comprise two to three atoms of zinc per six molecules of insulin lispro.

In particular aspects, the cake wash solution comprises a water miscible organic solvent, a crystal stabilizing agent, and a zinc salt wherein the solution has a pH that is about 4.5 to 8.5.

The present invention further provides a method for producing insulin lispro crystals with two to three zinc atoms per hexamer of insulin lispro comprising (a) providing a decanted crystal slurry comprising insulin lispro crystals, a water miscible organic solvent, a crystal stabilizing agent, and a zinc salt wherein the crystal slurry has a pH that is about 7.0 to 8.5; (b) adding a cake wash solution to the decanted crystal slurry to provide a mixture and incubating the mixture for a time sufficient to remove unbound zinc from the insulin lispro crystals, and (c) removing the cake wash solution from the mixture to provide the insulin lispro crystals with two to three zinc atoms per hexamer of insulin lispro.

In particular aspects, the decanted crystal slurry is applied to a filter apparatus prior to adding the cake wash solution. In particular aspects, the decanted crystal slurry is applied to a filter apparatus prior and formed into a crystal cake prior to adding the cake wash solution.

In particular aspects, the decanted crystal slurry has a zinc content greater than two to three zinc molecules per hexamer of insulin lispro. In particular aspects, after removing the cake wash solution the zinc content of the insulin lispro crystals is two zinc molecules per hexamer.

In particular aspects, after removing the cake wash solution the zinc content of the insulin lispro crystals is three zinc molecules per hexamer.

In particular aspects, the cake wash solution comprises a water miscible organic solvent, a crystal stabilizing agent, and zinc salt, wherein the solution has a pH that is about 4.5 to 8.5. In a further aspect, the pH of the cake wash solution is about 5.5.

In particular aspects, the water miscible organic solvent is selected from the group consisting of ethanol, methanol, acetone, and isopropanol. In particular aspects, the water miscible organic solvent is isopropanol. In particular aspects, the water miscible organic solvent is present in the decanted crystal slurry in an amount which corresponds to about 2.5% (v/v) to 9.0% (v/v) of the solution. In particular aspects, the cake wash solution further includes from about 0% (v/v) to about 10% (v/v) of the water miscible organic solvent. In a further aspect of the method, the cake wash solution comprises about 5.0% (v/v) of the water miscible organic solvent.

In particular aspects, the decanted crystal slurry comprises ammonium acetate, which may in particular aspects comprise ammonium acetate at a concentration of about 750 mM to 850 mM. In further embodiments, the ammonium acetate concentration is about 800 mM.

In particular aspects, the cake wash solution comprises ammonium acetate, which may in particular aspects comprise ammonium acetate at a concentration of about 200 mM to 800 mM. In further aspects, the ammonium acetate concentration is about 400 mM.

In particular aspects, the cake wash solution comprises about 400 mM acetate, about 5.0% (v/v) isopropanol, about 7 mM m-cresol, about 0.4 mM zinc chloride, at a pH of about 5.5.

In particular aspects, the crystal stabilizing agent is resorcinol, cresol, meta-cresol, methyl p-hydroxybenzoate, or methyl 4-hydroxybenzoate. In particular aspects, the crystal stabilizing agent is meta-cresol. In particular aspects, the decanted slurry comprises about 5 to mM or about 7.0 mM of the crystal stabilizing agent. In particular aspects, the cake wash solution comprises from about 5 to 10 mM of the crystal stabilizing agent. In particular aspects, the cake wash solution comprises about 7.0 mM of the crystal stabilizing agent. In particular aspects, the solution and the cake wash solution comprise the crystal stabilizing agent and excludes phenol. However, in particular aspects, the solution may include a trace amount of phenol.

In particular aspects, the zinc salt is zinc chloride.

In particular aspects, the insulin lispro crystals in step (c) are dried to provide the insulin lispro crystals with two to three zinc atoms per hexamer of insulin lispro.

The present invention further provides a method for preparing insulin lispro crystals with two to three zinc atoms per hexamer of insulin lispro, comprising (a) providing a solution comprising the insulin lispro, a water miscible organic solvent, and a crystal stabilizing agent, wherein the solution has a pH that is about 7.0 to 8.5; (b) adding a zinc salt to the solution to provide a crystallizing solution and incubating the crystallizing solution for a time sufficient produce insulin lispro crystals; (c) allowing the insulin lispro crystals in the solution to settle in the crystallizing solution and decanting the crystallizing solution from the settled insulin lispro crystals to produce a decanted crystal slurry; (d) applying the decanted crystal slurry to a filter apparatus to remove remaining crystallizing solution from the decanted crystal slurry to produce a crystal cake bed; (e) adding a cake wash solution to the decanted crystal slurry to provide a mixture and incubating the mixture for a time sufficient to remove unbound zinc from the insulin lispro crystals, and (f) removing the cake wash solution from the mixture to provide the insulin lispro crystals with two to three zinc atoms per hexamer of insulin lispro.

In particular aspects, the decanted crystal slurry has a zinc content greater than two to three zinc molecules per hexamer of insulin lispro. In particular aspects, after removing the cake wash solution the zinc content of the insulin lispro crystals is two zinc molecules per hexamer.

In particular aspects, after removing the cake wash solution the zinc content of the insulin lispro crystals is three zinc molecules per hexamer.

In particular aspects, the cake wash solution comprises a water miscible organic solvent, a crystal stabilizing agent, and zinc salt, wherein the solution has a pH that is about 4.5 to 8.5. In a further aspect, the pH of the cake wash solution is about 5.5.

In particular aspects, the water miscible organic solvent is selected from the group consisting of ethanol, methanol, acetone, and isopropanol. In particular aspects, the water miscible organic solvent is isopropanol. In particular aspects, the water miscible organic solvent is present in the decanted crystal slurry in an amount which corresponds to about 2.5% (v/v) to 9.0% (v/v) of the solution. In particular aspects, the cake wash solution further includes from about 0% (v/v) to about 10% (v/v) of the water miscible organic solvent. In a further aspect of the method, the cake wash solution comprises about 5.0% (v/v) of the water miscible organic solvent.

In particular aspects, the solution comprises ammonium acetate, which may in particular aspects comprise ammonium acetate at a concentration of about 750 mM to 850 mM. In further embodiments, the ammonium acetate concentration is about 800 mM.

In particular aspects, the cake wash solution comprises ammonium acetate, which may in particular aspects comprise ammonium acetate at a concentration of about 200 mM to 800 mM. In further embodiments, the ammonium acetate concentration is about 400 mM.

In particular aspects, the cake wash solution comprises about 400 mM acetate, about 5.0% (v/v) isopropanol, about 7 mM m-cresol, about 0.4 mM zinc chloride, at a pH of about 5.5.

In particular aspects, the crystal stabilizing agent is resorcinol, cresol, meta-cresol, methyl p-hydroxybenzoate, or methyl 4-hydroxybenzoate. In particular aspects, the crystal stabilizing agent is meta-cresol. In particular aspects, the solution comprises about 5 to mM or about 7.0 mM of the crystal stabilizing agent. In particular aspects, the cake wash solution comprises from about 5 to 10 mM of the crystal stabilizing agent. In particular aspects, the cake wash solution comprises about 7.0 mM of the crystal stabilizing agent. In particular aspects, the solution and the cake wash solution comprise the crystal stabilizing agent and excludes phenol. However, in particular aspects, the solution may include a trace amount of phenol.

In particular aspects, the zinc salt is zinc chloride.

In particular aspects, the insulin lispro crystals in step (f) are dried to provide the insulin lispro crystals with two to three zinc atoms per hexamer of insulin lispro.

The present invention further provides a crystalline insulin composition comprising insulin lispro, at least two and not more than three atoms of zinc per six molecules of the insulin lispro, and meta-cresol. In particular aspects, the crystalline insulin composition comprises insulin lispro, two or three atoms of zinc per six molecules of the insulin lispro, and meta-cresol. In particular aspects, the crystalline insulin composition comprises insulin lispro, two to three atoms of zinc per six molecules of the insulin lispro, and meta-cresol. In particular aspects, the crystalline insulin composition comprises insulin lispro, two atoms of zinc per six molecules of the insulin lispro, and meta-cresol. In particular aspects, the crystalline insulin composition comprises insulin lispro, three atoms of zinc per six molecules of the insulin lispro, and meta-cresol.

In further aspects, the present invention provides a method for preparing insulin or insulin analog crystals comprising: (a) providing a solution comprising the insulin or insulin analog, a water miscible organic solvent, and a crystal stabilizing agent, wherein the solution has a pH that is about 7.0 to 8.5; and (b) adding a zinc salt to the solution to provide a crystallizing solution and incubating the crystallizing solution for a time sufficient for the insulin or insulin analog to crystallize produce the insulin or insulin analog crystals.

In particular embodiments, the solution comprises an organic acid or salt selected from the group consisting of acetic acid, acetate, citric acid, citrate, and glycine. In particular embodiments, the organic acid or salt comprises acetate.

In particular embodiments, the solution comprises a base selected from the group consisting of potassium hydroxide, sodium hydroxide, and ammonium hydroxide. In particular embodiments, wherein the base comprises ammonium hydroxide.

In particular embodiments, the insulin or insulin analog comprises a concentration in the range of 1.5 g/L of 2.5 g/L.

In particular embodiments, wherein the water miscible organic solvent comprises ethanol, methanol, acetone, or isopropanol. In particular embodiments, the water miscible organic solvent comprises isopropanol. In particular embodiments, the water miscible organic solvent comprises an amount which corresponds to about 2% (v/v) to 10% (v/v) of the solution.

In particular embodiments, the crystal stabilizing agent comprises resorcinol, cresol, meta-cresol, methyl p-hydroxybenzoate, methyl 4-hydroxybenzoate, or phenol. In particular embodiments, the crystal stabilizing agent comprises meta-cresol. In particular embodiments, the crystal stabilizing agent comprises meta-cresol at a concentration not less than 3.5 mM.

In particular embodiments, the zinc salt comprises zinc acetate, zinc bromide, zinc chloride, zinc fluoride, zinc iodide, or zinc sulfate. In particular embodiments, the zinc salt comprises zinc chloride. In particular embodiments, the amount of zinc salt added to the solution is sufficient to provide at least two molecules of zinc per six molecules of insulin or insulin analog. In particular embodiments, the amount of zinc salt added to the solution comprises an amount sufficient to provide two to three molecules of zinc per six molecules of insulin or insulin analog.

In particular embodiments, the crystal stabilizing agent comprises meta-cresol and the solution further includes phenol at a concentration not more than 0.08 mM.

In particular embodiments, the crystal stabilizing agent comprises meta-cresol and the solution does not include phenol.

In particular embodiments, the crystallization comprises incubating the crystallizing solution at a temperature of about 2° C. to 30° C.

In particular embodiments, wherein the crystallization comprises incubating the crystallizing solution at a temperature of about 2° C. to 10° C.

In particular embodiments, the crystallization comprises incubating the crystallizing solution at a first temperature of about 22° C. to 28° C. followed by a second temperature of about 2° C. to 8° C.

In particular embodiments, the crystallization comprises incubating the crystallizing solution for about 4 to 8 hours.

In particular embodiments, following the crystallization of the insulin or insulin analog, a crystal slurry comprising the insulin or insulin analog crystals is produced by removing the crystallizing solution from the insulin or insulin analog crystals.

In particular embodiments, following the crystallization of the insulin or insulin analog, a crystal slurry comprising the insulin or insulin analog crystals is produced by (i) allowing the insulin or insulin analog crystals in the crystallizing solution to settle in the crystallizing solution and the crystallizing solution decanted from the settled insulin or insulin analog crystals or (ii) by centrifuging the crystallizing solution to remove the crystallizing solution from the insulin or insulin analog crystals.

In particular embodiments, the insulin or insulin analog crystals are allowed to settle for about five hours or more prior to decanting the crystallizing solution to produce the crystal slurry.

In particular embodiments, wherein the crystal slurry is applied to a filter apparatus to remove remaining crystallizing solution from the crystal slurry to produce a crystal cake bed and drying the crystal cake bed to provide the crystal insulin or insulin analog.

In particular embodiments, the crystal slurry is applied to a filter apparatus to remove remaining crystallizing solution from the crystal slurry to produce a crystal cake bed, washing the crystal cake bed with a cake wash solution comprising a water miscible organic solvent, a crystal stabilizing agent, and a zinc salt wherein the solution has a pH that comprises about 4.5 to 8.5, and drying the crystal cake bed to provide the crystal insulin or insulin analog.

In particular embodiments, the crystal slurry is applied to a centrifuge to remove remaining crystallizing solution from the crystal slurry, washing the crystals with a cake wash solution comprising a water miscible organic solvent, a crystal stabilizing agent, and a zinc salt wherein the solution has a pH that comprises about 4.5 to 8.5, and drying the crystals to provide the crystal insulin or insulin analog.

In particular embodiments, the water miscible organic solvent in the cake wash solution comprises about 0% to about 10% (v/v) of the cake wash solution.

In particular embodiments, the cake wash solution comprises no less than 0.2 M.

In particular embodiments, the cake wash solution comprises about 0.2 M to about 0.8 M acetate.

In particular embodiments, the cake wash solution comprises no less then 3.5 mM of the crystal stabilizing agent.

In particular embodiments, the cake wash solution comprises about 5 mM to about 10 mM of the crystal stabilizing agent.

In particular embodiments, the cake solution comprises about 0.2 to about 0.6 mM Zinc salt.

The present invention further provides a method for producing insulin or insulin analog crystals with 0.30% to 0.60% weight percent zinc (dried basis), or approximately two to three zinc atoms per hexamer of insulin or insulin analog, comprising: (a) providing a crystal slurry comprising insulin or insulin analog crystals, a water miscible organic solvent, a crystal stabilizing agent, and a zinc salt wherein the crystal slurry has a pH that is about 7.0 to 8.5; (b) adding a cake wash solution comprises a water miscible organic solvent, a crystal stabilizing agent, and a zinc salt, wherein the solution has a pH that is about 4.5 to 8.5 to the crystal slurry to provide a mixture and incubating the mixture for a time sufficient to remove unbound zinc from the insulin or insulin analog crystals, and (c) removing the cake wash solution from the mixture to provide the insulin or insulin analog crystals with two to three zinc atoms per hexamer of insulin or insulin analog.

In particular embodiments, the crystal slurry is applied to a centrifuge prior to adding the cake wash solution.

In particular embodiments, wherein the crystal slurry is applied to a filter apparatus prior to adding the cake wash solution.

In particular embodiments, the crystal slurry is applied to a filter apparatus and formed into a crystal cake prior to adding the cake wash solution.

In particular embodiments, after removing the cake wash solution the zinc content of the insulin or insulin analog crystals comprises two to three zinc molecules per hexamer.

In particular embodiments, after removing the cake wash solution the zinc content of the insulin or insulin analog crystals comprises 0.30% to 0.60% weight percent, calculated on the dried basis.

In particular embodiments, after removing the cake wash solution the zinc content of the insulin or insulin analog crystals comprises two zinc molecules per hexamer. In particular embodiments, after removing the cake wash solution the zinc content of the insulin or insulin analog crystals comprises three zinc molecules per hexamer.

In particular embodiments, the water miscible organic solvent in the decanted crystal slurry or cake wash solution comprises ethanol, methanol, acetone, or isopropanol. In particular embodiments, the water miscible organic solvent comprises isopropanol. In particular embodiments, the water miscible organic solvent in the cake wash solution is present in an amount which corresponds to about 0% (v/v) to 10% (v/v) of the cake wash solution.

In particular embodiments, the crystal stabilizing agent in the decanted crystal slurry or cake wash solution comprises resorcinol, cresol, meta-cresol, methyl p-hydroxybenzoate, methyl 4-hydroxybenzoate, or phenol. In particular embodiments, the crystal stabilizing agent comprises meta-cresol.

In particular embodiments, wherein the crystal stabilizing agent in the crystal slurry or cake wash solution does not include phenol. In particular embodiments, the crystal stabilizing agent in the crystal slurry or cake wash solution includes phenol at a concentration not more than 0.08 mM.

In particular embodiments, the zinc salt in the crystal slurry or cake wash comprises zinc acetate, zinc bromide, zinc chloride, zinc fluoride, zinc iodide, or zinc sulfate. In particular embodiments, the zinc salt in the crystal slurry or cake wash solution comprises zinc chloride. In particular embodiments, the zinc salt in the crystal slurry or cake wash solution comprises about 0.2 to about 0.6 mM.

In particular embodiments, the insulin or insulin analog crystals in step (c) are dried to provide the insulin or insulin analog crystals comprising 0.30% to 0.60% weight percent zinc (dried basis), or about two to three zinc atoms per hexamer of insulin or insulin analog.

The present invention further provides a method for preparing insulin or insulin analog crystals with 0.30% to 0.60% zinc content (dried basis), or about two to three zinc atoms per hexamer of insulin or insulin analog, comprising: (a) providing a solution comprising the insulin or insulin analog, a water miscible organic solvent, and a crystal stabilizing agent, wherein the solution has a pH that is about 7.0 to 8.5; (b) adding a zinc salt to the solution to provide a crystallizing solution and incubating the crystallizing solution for a time sufficient produce insulin or insulin analog crystals; (c) removing the crystallizing solution from the insulin or insulin analog crystals to produce a crystal slurry; (d) applying the crystal slurry to a filter apparatus or centrifuge to remove remaining crystallizing solution from the decanted crystal slurry to produce a crystal cake bed; (e) adding a cake wash solution comprises a water miscible organic solvent, a crystal stabilizing agent, and zinc salt, wherein the solution has a pH that is about 4.5 to 8.5 to the decanted crystal slurry to provide a mixture and incubating the mixture for a time sufficient to remove unbound zinc from the insulin or insulin analog crystals, and (f) removing the cake wash solution from the mixture to provide the insulin or insulin analog crystals with 0.30% to 0.60% weight percent zinc content (dried basis), or approximately two to three zinc atoms per hexamer of insulin or insulin analog.

In particular embodiments, after removing the cake wash solution the zinc content of the insulin or insulin analog crystals comprises 0.30% to 0.60% weight percent, calculated on the dried basis.

In particular embodiments, wherein after removing the cake wash solution the zinc content of the insulin or insulin analog crystals comprises two to three zinc molecules per hexamer. In particular embodiments, after removing the cake wash solution the zinc content of the insulin or insulin analog crystals comprises two zinc molecules per hexamer. In particular embodiments, after removing the cake wash solution the zinc content of the insulin or insulin analog crystals comprises three zinc molecules per hexamer.

In particular embodiments, the water miscible organic solvent in the solution or cake wash solution comprises ethanol, methanol, acetone, or isopropanol. In particular embodiments, the water miscible organic solvent comprises isopropanol.

In particular embodiments, the water miscible organic solvent in the cake wash solution comprises an amount which corresponds to about 0% (v/v) to 10.0% (v/v) of the cake wash solution. In particular embodiments, the water miscible organic solvent in the crystalizing solution comprises an amount which corresponds to about 2% (v/v) to 10% (v/v) of the solution.

In particular embodiments, the crystal stabilizing agent in the solution or cake wash solution comprises resorcinol, cresol, meta-cresol, methyl p-hydroxybenzoate, methyl 4-hydroxybenzoate, or phenol. In particular embodiments, the crystal stabilizing agent is meta-cresol.

In particular embodiments, the crystal stabilizing agent in the solution or cake wash solution does not include phenol.

In particular embodiments, the crystal stabilizing agent in the solution or cake wash solution includes phenol at a concentration not more than 0.08 mM.

In particular embodiments, the zinc salt in the crystallizing solution or cake wash solution comprises zinc acetate, zinc bromide, zinc chloride, zinc fluoride, zinc iodide, or zinc sulfate. In particular embodiments, the zinc salt in the crystallizing solution or cake wash solution comprises zinc chloride.

In particular embodiments, step (f) comprises drying the insulin or insulin analog crystals to provide the insulin or insulin analog crystals with 0.30% to 0.60% weight percent (dried basis) zinc content, or about two to three zinc atoms per hexamer of insulin or insulin analog.

In particular embodiments, the crystal slurry comprising the insulin or insulin analog crystals is produced by (i) allowing the insulin or insulin analog crystals in the crystallizing solution to settle in the crystallizing solution and the crystallizing solution decanted from the settled insulin or insulin analog crystals or (ii) by centrifuging the crystallizing solution to remove the crystallizing solution from the insulin or insulin analog crystals.

In particular embodiments, the insulin analog herein comprises insulin lispro.

The present invention further provides a crystalline composition comprising insulin or insulin analog, 0.30% to 0.60% zinc content (dried basis), or about two to three atoms of zinc per six molecules of the insulin or insulin analog, and meta-cresol.

In particular embodiments, the insulin crystals that are produced comprise a size of 10 μm or greater. In particular embodiments, the insulin or insulin analog comprises insulin lispro.

BRIEF DESCRIPTION OF THE DRAWINGS

FIG. 4A shows a representative X-ray diffraction image from a single crystal of insulin lispro. FIG. 4B difference Fourier map contoured at 3 rmsd (green). The side chains of His-B5 and surrounding protein atoms are shown as sticks. This Figure shows one of the two zinc sites in the asymmetric unit, each of which is chelated by three histidine side chains related by crystallographic symmetry.

DETAILED DESCRIPTION OF THE INVENTION

The present invention provides a method for crystallizing insulin or insulin analogs under alkaline conditions in the presence of zinc. The present invention has been exemplified with insulin lispro. Current methods for preparing insulin or insulin analogs such as insulin lispro crystals are usually performed at an alkaline pH from about 8.5 to about 9.5 in the absence of zinc (See U.S. Pat. No. 5,597,893) or at an acidic pH of about 5.5 to about 6.5 in the presence of zinc (See U.S. Pat. No. 5,504,188). However, we have found that insulin lispro may be crystallized at an alkaline pH that is at least one or more pH units greater than the pI of the insulin lispro in the presence of zinc and when they are crystallized using the method herein, large, ordered crystals of the insulin lispro are produced. These large insulin crystals may be recovered from the crystallization solution by filtration through a filter apparatus and then dried in the filter apparatus. In many current methods for producing insulin crystals, the crystals produced may be too small to be efficiently separated from the crystallization solution by filtration and other methods such as centrifugation are used to separate the crystals from the crystallization solution. The method disclosed herein is capable of producing a preparation of insulin or insulin analogs such as insulin lispro zinc hexamers with purity greater than about 99% and a yield of about 90% to 100% recovery of the insulin lispro.

Figure 3:
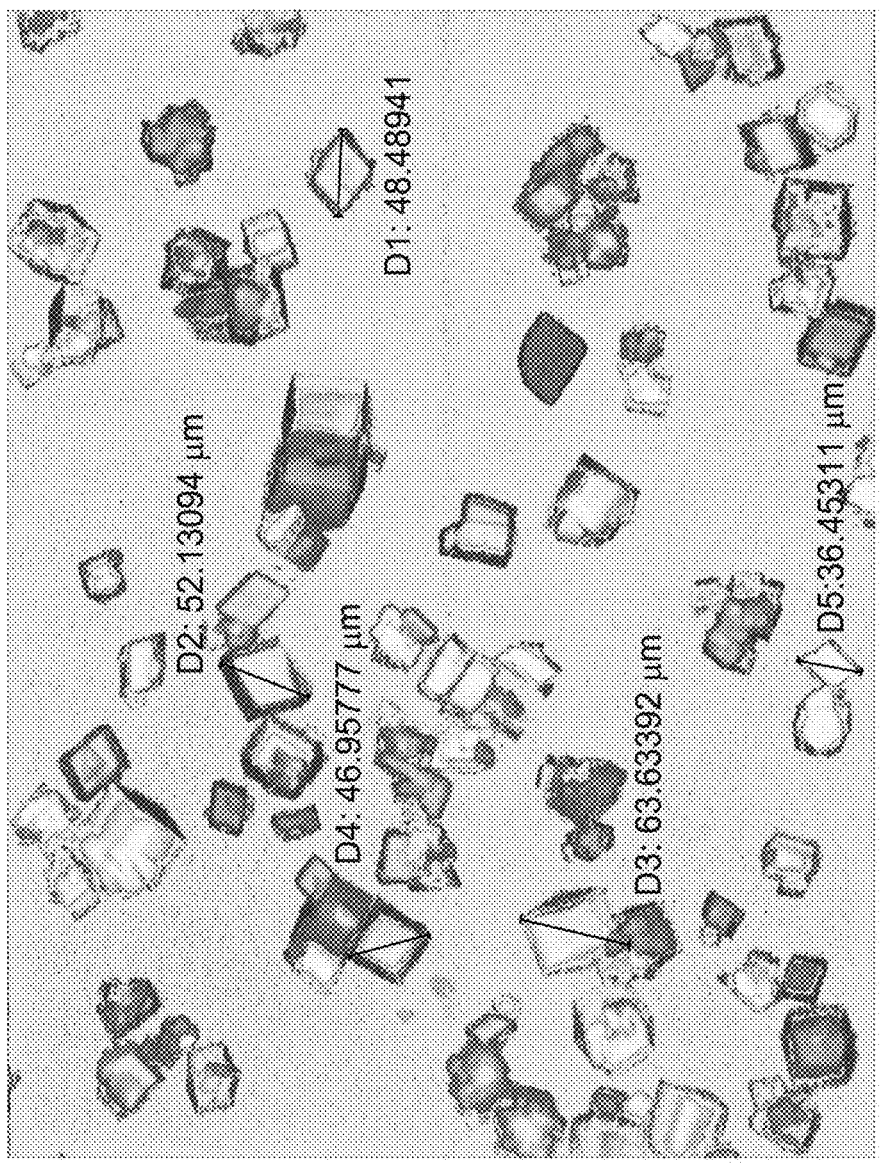
FIG. 3 shows a photomicrograph of insulin lispro crystals produced by the method disclosed herein.

An important aspect of the method disclosed here is that it enables the production of large insulin lispro crystals that are about 10 μm or greater in size in high yield (See for example, FIG. 3). The inventors have discovered that inducing crystallization of insulin lispro in a solution at a pH that is greater than the pI of the insulin lispro molecule facilitates the formation of insulin lispro crystals that are able to be separated from the crystallization solution by filtering through a filter apparatus and then dried in the same filter apparatus. An example of a filter apparatus suitable for filtering and drying the insulin lispro crystals is an agitated Nutsche filter apparatus. It was further found that by including a water miscible organic solvent (for example, isopropanol) in the crystallization solution, an enhanced rate of crystallization of the insulin lispro and the formation of the large insulin lispro crystals occurred.

In general, the insulin or insulin analog is crystallized in a solution comprising about 0.7 to 0.8 M ammonium acetate buffer, optionally a water miscible organic solvent, a crystal stabilizing agent, optionally a trace amount of phenol, and zinc salt solution in the correct ratios to target an insulin or insulin analog concentration of about 1 to 5 g/L for crystallization and the solution is mixed with a low shear marine impeller.

An important aspect of the invention is that the solution of insulin or insulin analog is prepared and the pH adjusted to a pH at least 1.5, 2, or 3 pH units greater than the pI of the insulin or insulin analog before the zinc salt is added to the solution to provide a crystallizing solution that induces crystallization of the insulin or insulin analog therein. The order the water miscible organic solvent and the crystal stabilizing agent are added to the insulin or insulin analog solution may be varied provided the pH of the solution is adjusted prior to the addition of the zinc salt. Thus, an aqueous solution of insulin or insulin analog is provided comprising or consisting essentially of about ammonium acetate, a water miscible organic solvent, and a crystal stabilizing agent.

The concentration of the insulin or insulin analog is about 1 to 5 g/L or about 2.2 g/L of insulin or insulin analog per liter of crystallizing solution. The ammonium acetate may be about 0.7 to 0.85 M or about 0.8 M. The water miscible organic solvent may be at a concentration of about 0% to 20% (v/v) or 1% to 5% (v/v) or about 3.6% (v/v). Representative examples of water miscible organic solvents include ethanol, methanol, acetone, glycerol, and isopropanol. In particular aspects, the water miscible organic solvent is isopropanol.

The crystal stabilizing agent may be at a concentration of about 5 to 10 mM or 6.8 to 7.2 mM and optionally, a trace amount of phenol at about 0.02 to 0.08 mM or about 0.05 to 0.07 mM. In particular aspects, the solution comprises about 7.0 mM of the crystal stabilizing agent. In particular aspects, the phenol is at about 0.060 mM. In particular aspects, the solution comprises about 5 to 10 mM or 6.8 to 7.2 mM of the crystal stabilizing agent and no phenol. The crystal stabilizing agent interacts with the insulin or insulin analog when the pH of the aqueous solution is adjusted to a pH that is greater than the pI of the insulin or insulin analog. Representative examples of crystal stabilizing agents include phenolic agents such as resorcinol, cresol, meta-cresol, methyl p-hydroxybenzoate, and methyl 4-hydroxybenzoate. In particular aspects, the crystal stabilizing agent is meta-cresol. Example 1 shows the crystallization of insulin or insulin analog in the presence of a trace amount of phenol. Example 2 shows the crystallization of insulin or insulin analog in the absence of a trace amount of phenol. A trace amount of phenol is a concentration of phenol that is greater than 0.08 mM.

The pH of the aqueous solution is adjusted to be at a pH that is at least 1, 2, 2.5, or 3 pH units greater than the pI of the insulin or insulin analog using a base such as ammonium hydroxide. In particular aspects the pH is adjusted to about 7.0 to about 8.5 or about pH 8.0 using a base such as 50% ammonium hydroxide. The crystal stabilizing agent interacts with the insulin or insulin analog at a pH that is greater than the pI of the insulin or insulin analog.

To initiate crystal formation, a defined amount of a zinc salt stock solution is added to the above solution in an amount sufficient to provide a crystallizing solution comprising about two to three zinc molecules per six molecules of insulin or insulin analog. Insulin or insulin analog will form a hexamer with two to three zinc molecules; this is the primary building component of crystals. Representative examples of zinc salts include zinc acetate, zinc bromide, zinc chloride, zinc fluoride, zinc iodide, and zinc sulfate. As an example, when the zinc salt is zinc chloride, the final zinc chloride concentration may be about 0.4 mM to every 2.2 grams of the insulin or insulin analog to initiate crystal formation. The slurry is allowed to mix and incubate for a defined time and temperature to further promote crystal formation. For example, the slurry may be incubated at about room temperature or 25° C. for about two hours and then for about eight hours at about 5° C.

During crystallization, a low shear, axial flow impeller (e.g., pitched-blade or marine impeller) may be used to provide just enough mixing power input to circulate the solution. After crystallization is complete, the agitation is stopped and the crystal slurry is allowed to gravity settle for a defined time, and a portion of the supernatant is decanted to reduce the filtration volume. In general, the insulin or insulin analog crystals will have settled within about four or more hours but the actual time may depend on the size of the crystallization vessel.

After crystallization, the entire volume of decanted crystal slurry is then transferred to a filter apparatus. An example of a suitable filter apparatus is an agitated Nutsche filter, which may have a composite sintered stainless steel screen with a pore size that is about 5 μm. The slurry is first gravity filtered, which allows a layer of cake to form on the composite screen with minimal breakthrough. After the target gravity filtrate volume is achieved, the filter apparatus is pressurized to about 0.0138 to 0.034 MPa (about 2 to about 10 psid) or 0.02 MPa (8 psid) with nitrogen to increase filtration flux. Initial filtration is complete when the target filtrate volume is collected, in general, about 89% to 91% or 90% of the crystal slurry filtered. When empty of slurry, the crystallization vessel is rinsed with a defined volume of cake wash solution. The defined volume may be about 4.5% to 5.5% of the initial crystallization volume.

The cake wash solution comprises a zinc salt, a water miscible organic solvent, and a crystal stabilizing agent in a buffer at pH of about 5.3 to 5.7 or about 5.5. In particular aspects, the cake wash solution may comprise about 0.2 to 0.6 mM zinc salt, which in particular aspects may be zinc chloride; about 0% to 10% (v/v) water miscible organic solvent, which in particular aspects may be isopropanol; 5.0 to 10.0 mM of a crystal stabilizing agent, which in particular aspects may be m-cresol; and, about 0.2 to 0.8 M acetate. In particular aspects, the cake wash solution may comprise about 0.38 to 0.42 mM zinc salt, which in particular aspects may be about 0.4 mM zinc chloride; about 4% to 6% (v/v) water miscible organic solvent, which in particular aspects may be isopropanol; 6.8 to 7.2 mM of a crystal stabilizing agent, which in particular aspects may be m-cresol; and, about 0.38 to 0.42 M acetate. In particular aspects, the cake wash solution may comprise about 0.4 mM zinc salt, which in particular aspects may be zinc chloride; about 5% (v/v) water miscible organic solvent, which in particular aspects may be isopropanol; 7.0 mM of a crystal stabilizing agent, which in particular aspects may be m-cresol; and, about 0.4 M acetate.

The acetate concentration and the pH of the crystallizing solution and the cake wash solution allow control of the zinc concentration in the crystals. In a particular aspects of the invention, the zinc concentration is slightly high in the crystallization solution, for example, a concentration sufficient to provide 3 to 4 zinc atoms per hexamer of insulin or insulin analog. During the cake wash, the concentration of zinc is reduced to 2 to 3 zinc atoms per hexamer of insulin or insulin analog. In a particular aspect, the zinc is reduced to 2 atoms of zinc per hexamer of insulin or insulin analog during the cake wash.

Following completion of the initial filtration, the vessel rinse is also transferred to the filter apparatus. The filter apparatus is again pressurized to about 0.0138 to 0.034 MPa (about 2 to about 10 psid) or about 20 MPa (8 psid) to remove liquid without allowing the liquid level to drop below the top of the cake bed. The filter cake is then washed a second time with a defined volume of cake wash solution. The defined volume may be about 4.5% to 5.5% of the initial crystallization volume. The filter apparatus is again pressurized to about 0.0138 to 0.034 MPa (about 2 to about 10 psid) or about 0.027 MPa (8 psid) to remove liquid without allowing the liquid level to drop below the top of the cake bed.

Following the second wash, the filter cake is dried. The filter drying may be accomplished using about 0.020 MPa to about 0.048 MPa (about 3 to about 7 psid, respectively) or 0.034 MPa (5 psid) of positive pressure above the cake. Positive pressure is maintained using dry nitrogen, which is regulated at the source. Once no liquid or foam is observed leaving the filter outlet, a vacuum in the range of about −400 to about −380 inches water column (about −747 to −709 mm Hg) or about −400 inches water column (about −747 mmHg or 14.6 psig) may be applied to increase the rate of drying. During drying, the entire cake is agitated with a vertical blade S-impeller, which is lowered into the cake. Drying proceeds until the cake has reached a target moisture content of less than 8%. The final crystallized drug substance is removed from the filter apparatus and packaged and stored until reconstituted.

The present invention is particularly useful for crystallizing insulin lispro. In general, the insulin lispro is crystallized in a solution comprising about 700 to 850 mM ammonium acetate buffer, optionally a water miscible organic solvent, a crystal stabilizing agent, optionally a trace amount of phenol, and zinc salt solution in the correct ratios to target an insulin lispro concentration of about 1 to 5 g/L for crystallization and the solution is mixed with a low shear marine impeller.

An important aspect of the invention is that the solution of insulin lispro is prepared and the pH adjusted to a pH at least 1.5, 2, or 3 pH units greater than the pI of the insulin lispro before the zinc salt is added to the solution to provide a crystallizing solution that induces crystallization of the insulin lispro therein. The order the water miscible organic solvent and the crystal stabilizing agent are added to the insulin lispro solution may be varied provided the pH of the solution is adjusted prior to the addition of the zinc salt. Thus, an aqueous solution of insulin lispro is provided comprising or consisting essentially of about ammonium acetate, a water miscible organic solvent, and a crystal stabilizing agent.

The concentration of the insulin lispro is about 1 to 5 g/L or about 2.2 g/L of insulin lispro per liter of crystallizing solution. The ammonium acetate may be about 0.7 to 0.85 M or about 0.8 M. The water miscible organic solvent may be at a concentration of about 0% to 20% (v/v) or 1% to 5% (v/v) or about 3.6% (v/v). Representative examples of water miscible organic solvents include ethanol, methanol, acetone, glycerol, and isopropanol. In particular aspects, the water miscible organic solvent is isopropanol.

The crystal stabilizing agent may be at a concentration of about 5 to 10 mM or 6.8 to 7.2 mM and optionally, a trace amount of phenol at about 0.02 to 0.08 mM or about 0.05 to 0.07 mM. In particular aspects, the solution comprises about 7.0 mM of the crystal stabilizing agent. In particular aspects, the phenol is at about 0.060 mM. In particular aspects, the solution comprises about 5 to 10 mM or 6.8 to 7.2 mM of the crystal stabilizing agent and no phenol. The crystal stabilizing agent interacts with the insulin lispro when the pH of the aqueous solution is adjusted to a pH that is greater than the pI of the insulin lispro. Representative examples of crystal stabilizing agents include phenolic agents such as resorcinol, cresol, meta-cresol, methyl p-hydroxybenzoate, and methyl 4-hydroxybenzoate. In particular aspects, the crystal stabilizing agent is meta-cresol. Example 1 shows the crystallization of insulin lispro in the presence of a trace amount of phenol. Example 2 shows the crystallization of insulin lispro in the absence of a trace amount of phenol. A trace amount of phenol is a concentration of phenol that is greater than 0.08 mM.

The pH of the aqueous solution is adjusted to be at a pH that is at least 1, 2, 2.5, or 3 pH units greater than the pI of the insulin lispro using a base such as ammonium hydroxide. In particular aspects the pH is adjusted to about 7.0 to about 8.5 or about pH 8.0 using a base such as 50% ammonium hydroxide. The crystal stabilizing agent interacts with the insulin lispro at a pH that is greater than the pI of the insulin lispro.

To initiate crystal formation, a defined amount of a zinc salt stock solution is added to the above solution in an amount sufficient to provide a crystallizing solution comprising about two to three zinc molecules per six molecules of insulin lispro. Insulin lispro will form a hexamer with two to three zinc molecules; this is the primary building component of crystals. Representative examples of zinc salts include zinc acetate, zinc bromide, zinc chloride, zinc fluoride, zinc iodide, and zinc sulfate. As an example, when the zinc salt is zinc chloride, the final zinc chloride concentration may be about 0.4 mM to every 2.2 grams of the insulin lispro to initiate crystal formation. The slurry is allowed to mix and incubate for a defined time and temperature to further promote crystal formation. For example, the slurry may be incubated at about room temperature or 25° C. for about two hours and then for about eight hours at about 5° C.

During crystallization, a low shear, axial flow impeller (e.g., pitched-blade or marine impeller) may be used to provide just enough mixing power input to circulate the solution. After crystallization is complete, the agitation is stopped and the crystal slurry is allowed to gravity settle for a defined time, and a portion of the supernatant is decanted to reduce the filtration volume. In general, the insulin lispro crystals will have settled within about four or more hours but the actual time may depend on the size of the crystallization vessel.

After crystallization, the entire volume of decanted crystal slurry is then transferred to a filter apparatus. An example of a suitable filter apparatus is an agitated Nutsche filter, which may have a composite sintered stainless steel screen with a pore size that is about 5 μm. The slurry is first gravity filtered, which allows a layer of cake to form on the composite screen with minimal breakthrough. After the target gravity filtrate volume is achieved, the filter apparatus is pressurized to about 0.0138 to 0.034 MPa (about 2 to about 10 psid) or 0.02 MPa (8 psid) with nitrogen to increase filtration flux. Initial filtration is complete when the target filtrate volume is collected, in general, about 89% to 91% or 90% of the crystal slurry filtered. When empty of slurry, the crystallization vessel is rinsed with a defined volume of cake wash solution. The defined volume may be about 4.5% to 5.5% of the initial crystallization volume.

The cake wash solution comprises a zinc salt, a water miscible organic solvent, and a crystal stabilizing agent in a buffer at pH of about 5.3 to 5.7 or about 5.5. In particular aspects, the cake wash solution may comprise about 0.2 to 0.6 mM zinc salt, which in particular aspects may be zinc chloride; about 0% to 10% (v/v) water miscible organic solvent, which in particular aspects may be isopropanol; 5.0 to 10.0 mM of a crystal stabilizing agent, which in particular aspects may be m-cresol; and, about 0.2 to 0.8 M acetate. In particular aspects, the cake wash solution may comprise about 0.38 to 0.42 mM zinc salt, which in particular aspects may be about 0.4 mM zinc chloride; about 4% to 6% (v/v) water miscible organic solvent, which in particular aspects may be isopropanol; 6.8 to 7.2 mM of a crystal stabilizing agent, which in particular aspects may be m-cresol; and, about 0.38 to 0.42 M acetate. In particular aspects, the cake wash solution may comprise about 0.4 mM zinc salt, which in particular aspects may be zinc chloride; about 5% (v/v) water miscible organic solvent, which in particular aspects may be isopropanol; 7.0 mM of a crystal stabilizing agent, which in particular aspects may be m-cresol; and, about 0.4 M acetate.

The acetate concentration and the pH of the crystallizing solution and the cake wash solution allow control of the zinc concentration in the crystals. In a particular aspects of the invention, the zinc concentration is slightly high in the crystallization solution, for example, a concentration sufficient to provide 3 or 4 zinc atoms per hexamer of insulin lispro. During the cake wash, the concentration of zinc is reduced to 2 or 3 zinc atoms per hexamer of insulin lispro. In a particular aspect, the zinc is reduced to 2 atoms of zinc per hexamer of insulin lispro during the cake wash.

Following completion of the initial filtration, the vessel rinse is also transferred to the filter apparatus. The filter apparatus is again pressurized to about 0.0138 to 0.034 MPa (about 2 to about 10 psid) or about 20 MPa (8 psid) to remove liquid without allowing the liquid level to drop below the top of the cake bed. The filter cake is then washed a second time with a defined volume of cake wash solution. The defined volume may be about 4.5% to 5.5% of the initial crystallization volume. The filter apparatus is again pressurized to about 0.0138 to 0.034 MPa (about 2 to about 10 psid) or about 0.027 MPa (8 psid) to remove liquid without allowing the liquid level to drop below the top of the cake bed.

Following the second wash, the filter cake is dried. The filter drying may be accomplished using about 0.020 MPa to about 0.048 MPa (about 3 to about 7 psid, respectively) or 0.034 MPa (5 psid) of positive pressure above the cake. Positive pressure is maintained using dry nitrogen, which is regulated at the source. Once no liquid or foam is observed leaving the filter outlet, a vacuum in the range of about −400 to about −380 inches water column (about −747 to −709 mm Hg) or about −400 inches water column (about −747 mmHg or 14.6 psig) may be applied to increase the rate of drying. During drying, the entire cake is agitated with a vertical blade S-impeller, which is lowered into the cake. Drying proceeds until the cake has reached a target moisture content of less than 8%. The final crystallized drug substance is removed from the filter apparatus and packaged and stored until reconstituted.

In general the method disclosed herein will produce insulin or insulin analog crystals that have an average diameter equal to or greater than 10 μm. These crystals are amendable to drying on a filter with a pore size of about 5 μm. Adjusting the parameters of the method disclosed herein may produce crystals that have an average diameter less than 10 μm. These smaller crystals may be dried on filters having a pore size less than 5 μm. Thus, the present invention further provides a method for producing crystals of insulin or insulin analog wherein the insulin or insulin analog crystals are separated from the crystallizing solution by gravity and decanting the crystallizing solution to provide a crystal slurry, which is applied to the filter or screen in a filter apparatus such as a Nutsche filter apparatus to remove any remaining crystallizing solution to produce a crystal cake that is dried on the same apparatus wherein the pore size of the filter or screen in the filter apparatus is sufficient to prevent passage of the crystals without clogging filter.

We have found that for best stability of the crystalline drug substance and the utility of drug substance in formulating the commercial product, the insulin or insulin analog and the zinc should be present in a mole ratio of two $Zn^{2+}$ atoms per insulin hexamer or three $Zn^{2+}$ atoms per insulin hexamer, and the phenolic content should be almost exclusively m-cresol. For the best stability of the crystals and their utility in formulation of the commercial product, the crystalline drug substance should contain at least two but not more than three mole of $Zn^{2+}$ per six mole of insulin or insulin analog, and the phenolic content should be almost exclusively m-cresol. Higher amounts of $Zn^{2+}$ or significant amounts of phenolic components other than m-cresol, e.g., phenol, may require a buffer exchange to enable further processing of the crystals into the commercial formulation. A significant amount of phenolic components other than m-cresol is an amount that is greater than a trace amount, for example, a concentration of the phenolic components other than m-cresol that is greater than 0.08 mM.

Figure 1:
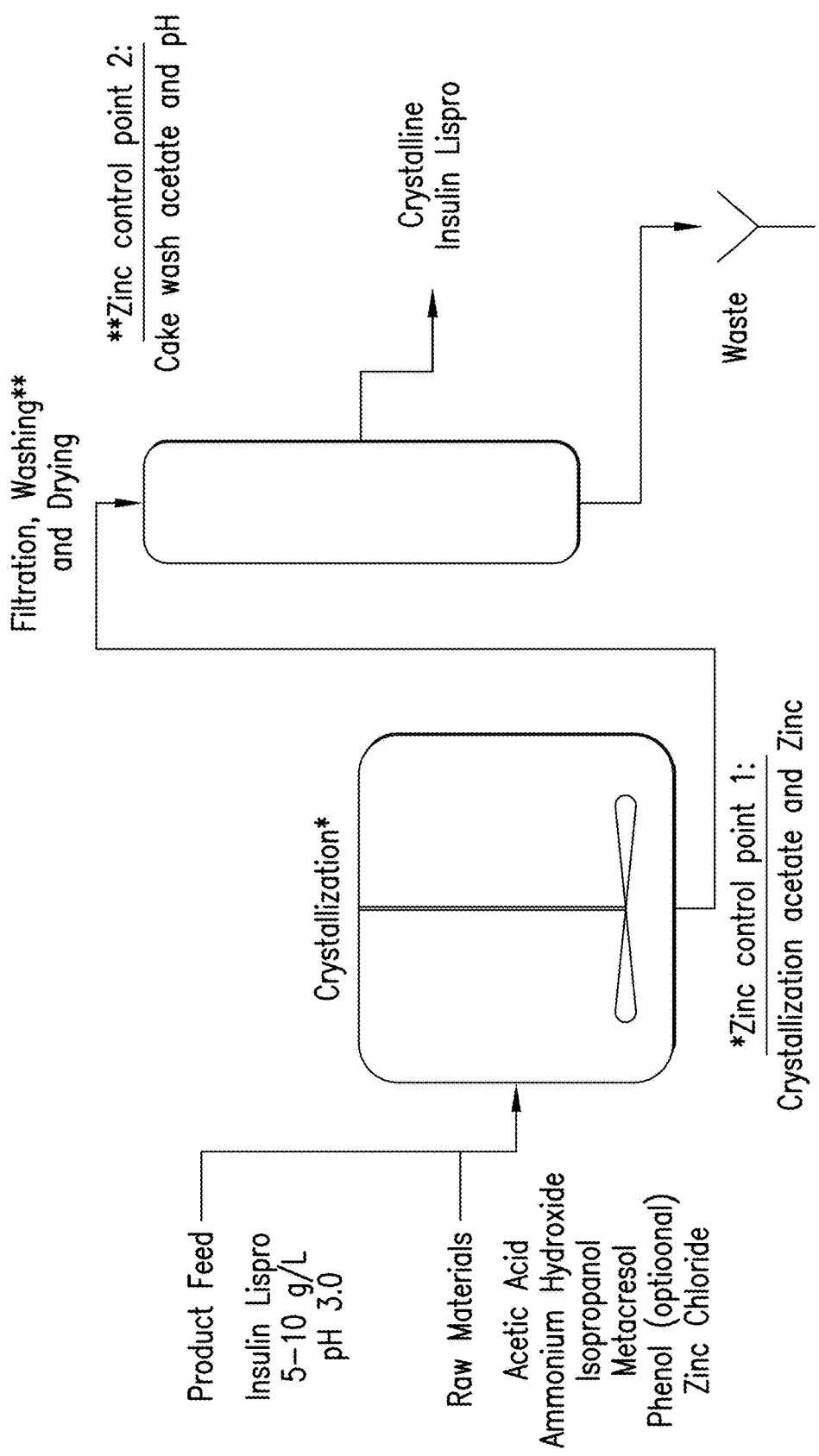
FIG. 1 shows a schematic representation of the Insulin lispro crystallization and filter drying process flow.

The present invention further provides a novel insulin lispro crystallization process in which zinc content is tunable through crystallization and filter drying process parameters. The process resulted in large crystals amenable to filtration at high filter loadings (up to 35 kg/m$^2$), allowing the development of a filter drying process (FIG. 1). Redundant control points for zinc content were built into the process at both the crystallization and the cake wash steps, consistently resulting in 2.5 zinc atoms per insulin lispro hexamer in dried crystalline product. This level is amenable to zinc supplementation during compounding to achieve the target ratio of 3.0 zinc atoms per hexamer. The combined crystallization and filter drying process was scalable and reproducible, with commercially viable process yields achieved at 40 g pilot scale.

The process we developed includes several key features that are distinct from previously described lispro crystallization processes. Most notably, the crystallization process is initiated by zinc and is performed at alkaline pH. Operating at alkaline conditions provides flexibility for process fit considerations and also mitigates formation of the A21 desamido degradate, which forms in acidic conditions. Inclusion of zinc in the crystallization process, if well controlled, allows for a streamlined, integrated process for compounding crystalline insulin lispro to generate a pharmaceutically useful preparation. Another key difference was the role of temperature. In previous crystallization processes, the role of temperature was described as not being important. However, we found that in the alkaline zinc process, a reduction in temperature from approximately 25° C. to approximately 5° C. caused crystallization to proceed rapidly and reach completion within 8 hours (FIG. 2), resulting in a short overall processing time suitable for commercial manufacturing. An additional difference is the selection of phenolic compounds. In the previously described insulin lispro crystallization process, the variation of the phenolic preservative caused changes in the crystal form. In the previously described zinc crystallization process, no crystals were observed when meta-cresol was used as the phenolic preservative. However, in the zinc alkaline crystallization process, rhombohedral crystals are obtained in the presence of 7 mM meta-cresol with or without 60 μM phenol.

Figure 4B:
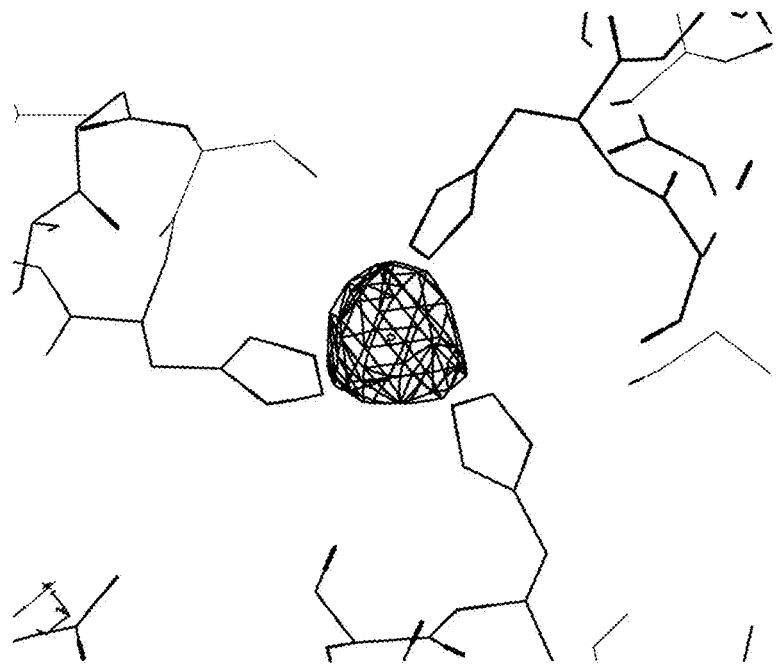
FIGS. 4A and 4B shows insulin lispro x-ray crystallography.
Figure 4A:
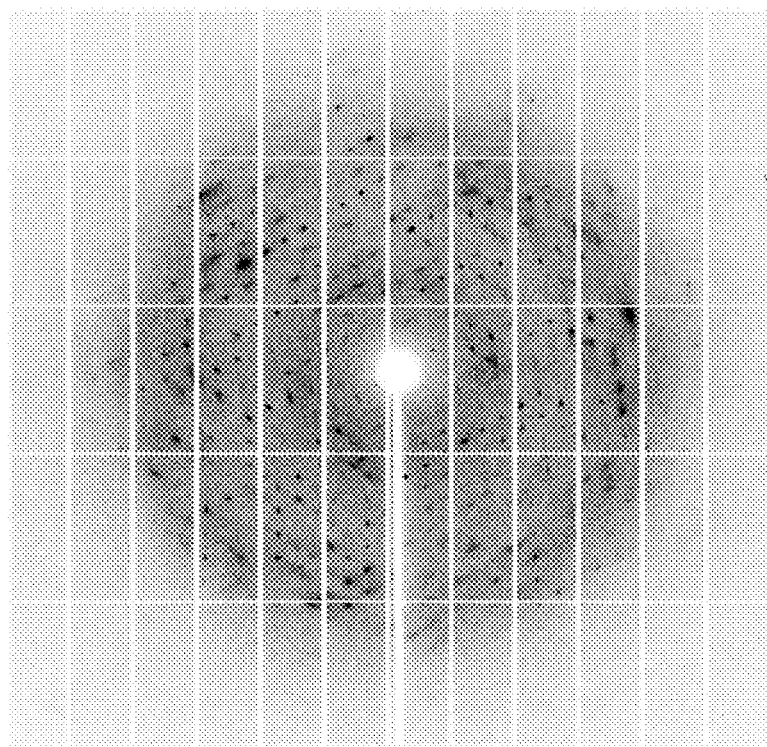

The published crystal structure of insulin lispro is a $T_3R_3$ hexamer isomorphous with the $T_3R_3$ crystal form of human insulin and containing two zinc atoms and three phenol molecules per hexamer (Ciszak et al., Op. cit.). The crystallization process described in this report also results in a rhombohedral crystal form containing hexameric lispro with two ordered zinc atoms (FIGS. 3 and 4A and 4B), consistent with the published structure (Ciszak et al., Op. cit.). The presence of additional zinc, in excess of two per hexamer and unable to be removed during filter drying, may result from off-axial zinc binding. The $T_3R_3$ human insulin structure has also been referred to as '4Zn insulin' due to off-axial binding of zinc atoms to histidines at positions 5 and 10 of the B-chain (Kaarsholm et al., Biochemistry 1989, 28, 4427-4435), resulting in three partially occupied zinc binding sites in addition to the two fully occupied ordered zinc binding sites (Derewenda et al., Op. cit.). Although the total zinc occupancy reported for $T_3R_3$ human insulin is 2.67 zinc atoms per hexamer (Smith et al., Op. cit.), structural differences between human insulin and insulin lispro may allow the lispro hexamer to accommodate greater off-axial zinc binding. In addition, the impact of acetic acid level during crystallization on zinc content of crystalline lispro (FIG. 5, FIGS. 6A and 6B, and Table 2) may indicate that the organic acid content during crystallization causes structural perturbations that influence off-axial zinc binding. The presence of off-axial zinc would be consistent with the observation that a portion of zinc could be removed by washing the crystal slurry at pH 5.5 (Table 3). The imidazole side chain of histidine has a pKa of approximately 6.0, and below this pH histidines could become protonated, disrupting the coordination of off-axial zinc (Zhou et al., Journal of Physical Chemistry B 2013, 117, 8954-8965).

The following examples are intended to promote a further understanding of the present invention.

EXAMPLE 1

This example illustrates the preparation of insulin lispro crystals obtained from a crystallization solution containing a trace amount of phenol.

After determining the concentration of the insulin lispro in an aqueous solution, the crystallization diluent is prepared in the crystallization vessel.

Water, glacial acetic acid, and isopropanol are initially added to a crystallization vessel and mixed, followed by adding m-cresol and phenol. Mixing is achieved using a low shear hydrofoil-type impeller. All additions to the crystallization diluent are made in the appropriate ratios to target the final component concentrations of about 3.0% (v/v) isopropanol, about 0.8 M acetate, about 7.0 mM m-cresol, about 60 μM phenol, and about 2.2 g/L insulin lispro for the crystallization reaction. The pH of the crystallization diluent is then adjusted to about 8.0 using ammonium hydroxide as the titrant.

Next, the aqueous solution comprising the insulin lispro is added to the crystallization vessel at a controlled rate. The aqueous solution is warmed to 25° C. immediately prior to transfer to the crystallization vessel. The pH of the reaction is continuously monitored and is titrated with ammonium hydroxide as needed to maintain a pH above 7.5. After addition is complete, agitation is continued for 5 to 10 minutes to ensure complete mixing, and the agitation rate is then decreased to a rate that provides just enough mixing power input to circulate the crystallization slurry.

A defined amount of a 3% zinc chloride stock solution sufficient to provide about 0.4 mM zinc is then added to the aqueous solution to initiate crystal formation. The temperature of the reaction is maintained at 25° C. for 2 hours, after which the temperature is decreased to 5° C. After crystallization is complete, within 4-8 hours after initiating the temperature decrease to 5° C., agitation is stopped and the crystals are allowed to gravity settle. A portion of the mother liquors is decanted to about 10% of the crystallization volume (approximately 240 L).

The entire crystallization slurry is then transferred to the filter dryer (FD-6830, 0.1 m$^2$), which contains a composite sintered 5 μm stainless steel screen installed per the vendor recommendation. The slurry is first gravity filtered, allowing a layer of cake to form on the composite screen. After the target gravity filtrate volume is achieved, the filter dryer is pressurized with nitrogen to increase filtration flux. Initial filtration is stopped after the crystallizer is emptied and at a point so as to maintain a liquid level above the cake in the filter dryer. When empty of slurry, the crystallization vessel is rinsed with a Cake Wash Solution at about 5° C. and comprising about 0.4 M acetate, about 7.0 mM m-cresol, about 0.40 mM zinc chloride, and 5% (v/v) isopropanol at a pH of about 5.0 through a dip tube to maximize product recovery and wash the filtration cake. The volume of cake wash solution added is about 5% of the pre-decanted crystallization batch volume and is transferred to the filter dryer. The filter dryer is again pressurized with nitrogen. The wash is complete when all liquid is removed from the filter dryer and foam is observed exiting the filter outlet.

Following the wash, the filter cake is dried using nitrogen under positive pressure above the cake. Positive pressure is maintained using dry nitrogen. When no liquid or foam is observed leaving the filter outlet, vacuum pressure can be applied to increase the rate of drying. During drying, the cake is agitated only after determining the "ball phase" has passed. The ball phase is the point during drying where if the bed were disturbed, the crystals would not break apart, but would instead agglomerate together into a sticky ball, destroying the crystalline nature of the material and converting it into a sticky amorphous precipitate. Ultimately, the on-set of agitation will be based on the Relative Humidity (RH) and/or temperature reading from the effluent stream. During drying, the process is paused to allow sampling for moisture (via KF) analysis. If the sample meets the moisture target (less than or equal to 8%), drying is considered complete and the final crystalline insulin lispro is removed from the dryer, packaged and placed into storage.

EXAMPLE 2

This example illustrates the preparation of insulin lispro crystals obtained from a crystallization solution that does not contain phenol.

A process stream containing 1.11 grams of insulin lispro at 8.51 g/L in 50 mM acetic acid, 10% v/v isopropanol, pH 2.9, is diluted into a crystallization diluent containing ammonium acetate, 2-propanol and m-cresol, pH 8.12. The crystallization diluent is a mixture of 26.17 mL of 14 M acetic acid, 277.0 mL of 100 mM acetic acid, 3.2 mL of isopropanol, and 0.36 mL of m-cresol which is adjusted to pH 8.10 using ammonium hydroxide. After addition of the product stream, the pH of the mixture is 7.76 at room temperature. Final component concentrations in the crystallization reaction are 0.82 M acetate, 0.65% v/v isopropanol, and 6.96 mM m-cresol. The crystallization is then initiated by addition of 0.4 mL of 3% w/v zinc chloride solution (final zinc chloride concentration 0.18 mM). The mixture is agitated at 25° C. for two hours, and then further agitated as the reaction temperature is reduced to 5° C. at a rate of 0.12° C./min. The crystal slurry is then aged at least 8 hours at 2-8° C. with agitation.

At the end of the age phase, the crystal slurry is allowed to gravity settle and 83% of the reaction volume is decanted. Crystal formation is confirmed by microscopic analysis and crystals are observed to be birefringent, with cubic shape and 20-30 µm average crystal size. The concentrated crystal slurry is filtered and dried under vacuum with a nitrogen sweep. The 1.05 g of dried crystals were obtained, corresponding to a crystallization yield of 95% (wet basis).

EXAMPLE 3

Process fit considerations led us to pursue an alternative crystallization process for insulin lispro distinct from those previously described. Specifically, we sought to develop a zinc crystallization process operable at alkaline pH with robust process controls for zinc content. Numerous options were available for each of the key materials—organic acid, alkaline titrant, organic solvent, phenolic stabilizer, and zinc salt. Ultimately, raw materials were selected because they were already used upstream of the crystallization process, thereby avoiding the introduction of a new raw material.

Crystallization and filter drying process. An overview of the crystallization process flow is shown in FIG. 1. Prior to initiating crystallization, a diluent consisting of water, acetic acid, isopropyl alcohol, meta-cresol, and phenol is prepared and mixed. Meta-cresol constitutes approximately 99% of the total phenolic stabilizer in the base process, with phenol accounting for the remainder, although it was also demonstrated that phenol could be removed altogether. Raw material additions are calculated to achieve the target crystallization concentrations shown in Table 1. After all components are added and mixed, the diluent is titrated to approximately pH 8.0 using ammonium hydroxide and the purified insulin lispro product feed is then added to the diluent with continued agitation.

TABLE 1

Target component concentrations for insulin lispro crystallization.

| Component | Target Concentration |
| --- | --- |
| Acetic acid | 0.8M |
| Insulin lispro | 2.2 g/L |
| Isopropyl alcohol | 3% (v/v) |
| Meta-cresol | 7 mM |
| Phenol | 60 µM |
| Zinc chloride | 0.40 mM |

The product feed typically contains approximately 5-10 g/L protein in dilute acetic acid and may be cooled to 2-8° C. to mitigate deamidation. The acidic product instantly transitions across its isoelectric point as it is added to the alkaline crystallization diluent. The rate of product addition is controlled to ensure the product remains in solution and the pH is titrated with ammonium hydroxide as needed to maintain pH above 7.5. After product addition is complete, agitation is then decreased to a rate that provides just enough mixing power input to circulate the crystallization slurry. A zinc chloride stock solution is then added to initiate crystal formation. The temperature of the reaction is initially maintained at approximately 25° C., after which the temperature is decreased to approximately 5° C. Within 4 hours after initiating the temperature decrease to 5° C., crystallization is essentially complete and agitation can be stopped to allow the crystals to gravity settle.

From the settled slurry, a portion of the mother liquors is decanted in order to reduce the filtration volume and remove fines. The decanted slurry is then transferred to a filter dryer with a composite sintered stainless steel screen (5-10 µm pore size). The slurry is initially gravity filtered to allow a layer of cake to form on the filter screen. The filter dryer is then pressurized with nitrogen to increase filtration flux. Filter loadings up to 35 kg/m2 have been demonstrated.

After filtration is completed, the crystal cake is washed with a volume of cake wash solution equivalent to 5-10% of the pre-decanted crystallization batch volume. The filter dryer is again pressurized with nitrogen during the cake wash to increase flux. When the wash is complete, the filter cake is dried using vacuum with agitation. The cake is periodically sampled and when the desired moisture content is achieved, drying is considered complete and the dried crystalline product is collected from the filter dryer and packaged.

Processing equipment varied according to the scales used. Crystallization studies were performed in glass (500 mL and 4 L) and stainless steel (25 L) jacketed vessels. Filter drying studies were performed using a jacketed glass tube (250 mL volume) with a stainless steel assembly, polytetrafluoroethylene gaskets, and a sintered stainless steel filter screen (5 cm2). For both crystallization and filter drying, temperature control was achieved via recirculating heater/chillers. When operating at 500 mL crystallization scale or smaller, crystals could alternatively be filtered without a washing step using a Buchner funnel and Whatman filter paper (#2, 8 μm pore size) and dried in a vacuum oven.

Insulin lispro content. Insulin lispro content was determined by a reverse-phase ultra performance liquid chromatography method. The method used water as aqueous phase and acetonitrile as organic phase, both of which contained dilute trifluoroacetic acid as counter-ion, and a C18 column. Insulin lispro was quantified against a pharmacopeial insulin lispro reference standard or a commercially available insulin lispro preparation. Samples in solid form were reconstituted in dilute hydrochloric acid for testing.

Zinc content. Zinc content in insulin lispro samples was determined by inductively coupled plasma atomic emission spectroscopy (ICP-AES). Zinc was quantified against a standard curve generated from a certified zinc standard traceable to the National Institute of Standards and Technology (NIST). Samples in solid form were reconstituted in dilute hydrochloric acid for testing.

Metacresol content. Metacresol content in insulin lispro samples was determined by a reverse-phase high performance liquid chromatography method. The method used a phosphate buffered aqueous phase, an acetonitrile based organic phase, and a C18 column. Metacresol was quantified against a pharmacopeial metacresol reference standard prepared at a known concentration. Samples in solid form were reconstituted in dilute hydrochloric acid for testing.

Loss on drying. Volatile mass fraction was determined by accurately weighing insulin lispro samples before and after drying at 105° C. for 16 hours.

Particle analysis. Real-time crystallization kinetics were monitored in situ using focused beam reflectance measurement (FBRM) (Kumar et al., AAPS PharmSciTech 2013, 14, (523-530).). Particle size distributions of dry powder insulin lispro samples were determined using laser diffraction. Powder samples for laser diffraction analysis were suspended in Isopar™ G containing 0.25% (w/v) lecithin.

X-ray analysis. A single crystal of insulin lispro, approximately 50 μm in each dimension, was transferred into 10 μL of phenol-free mother liquor supplemented with 30% (v/v) ethylene glycol for 30 sec before plunging into liquid nitrogen. X-ray diffraction data were collected at beamline 17-ID (IMCA-CAT) at the Advanced Photon Source (Argonne, Ill.) using an incident X-ray wavelength of 1 Å and a PILATUS 6M detector. Diffraction data were processed using the software autoPROC (Vonrhein et al., (2011), *Acta Cryst*. D67, 293-302) and XDS (Kabsch (2010) *Acta Cryst*. D66, 125-132). The structure was solved by molecular replacement using the software MOLREP (Collaborative Computational Project, Number 4. (1994). The CCP4 Suite: Programs for Protein Crystallography. *Acta Cryst*. D50, 760-763.; Vagin & Teplyakov, MOLREP: an automated program for molecular replacement. (1997) *J. Appl. Cryst*. 30, 1022-1025). Crystallographic refinement and electron density map calculations were performed using the software autoBUSTER (Bricogne et al., (2011). BUSTER version 2.11.4. Cambridge, United Kingdom: Global Phasing Ltd.) Visualization of electron density and coordinates was performed using Coot (Emsley et al., (2010) *Acta. Cryst*. D66, 486-501).

Light microscopy. Samples of crystal slurry were placed onto glass microscope slides and observed using a Nikon Eclipse E600 light microscope with 4× or 10× objective. A polarizing filter was used to visualize birefringent insulin lispro crystals.

Statistical analysis. Statistical significance was assessed by analysis of variance and two-tailed Student's t test. Differences were considered significant if they exhibited p values <0.05 in the Student's t test. Data analyses were performed using Microsoft Excel and JMP.

Figure 2:
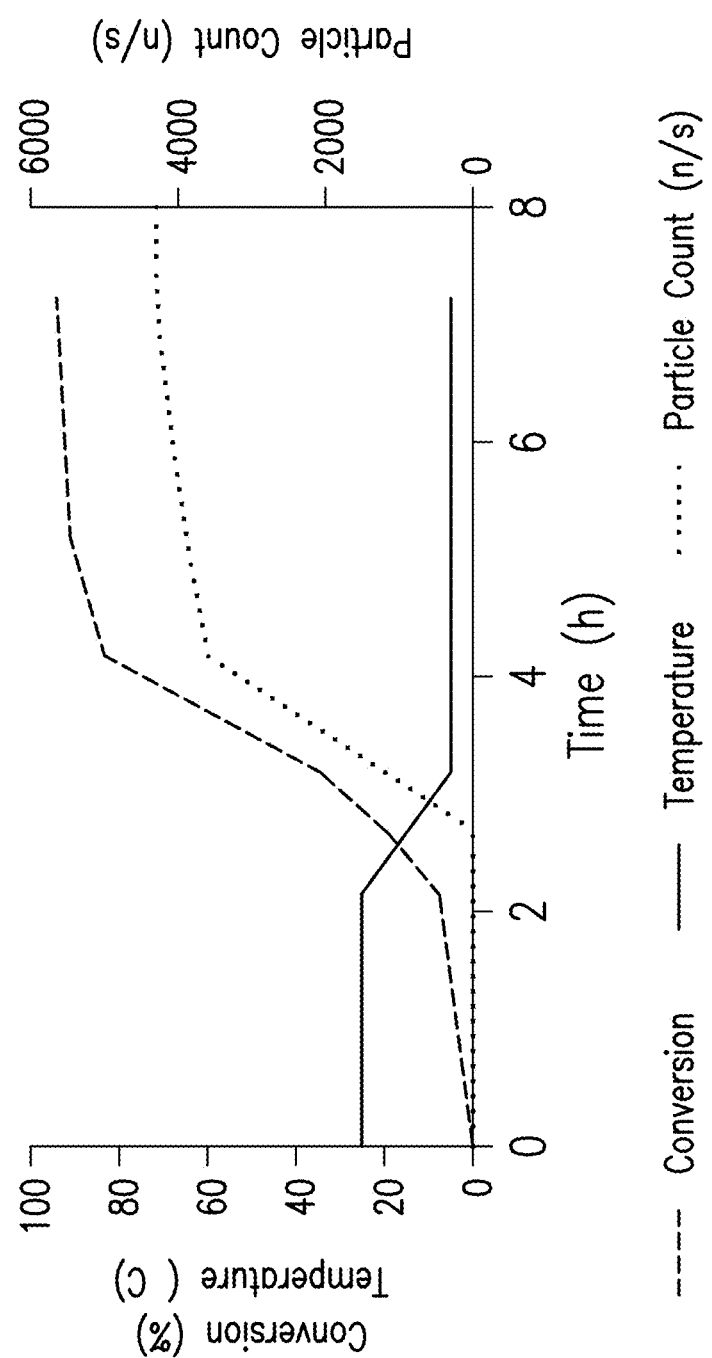
FIG. 2 shows the influence of temperature on crystallization kinetics of insulin lispro. After an initial 2 hour incubation at approximately 25° C., reduction in temperature to approximately 5° C. significantly accelerates the rate of crystal formation, reaching completion within 2-4 hours of the temperature change. Conversion is measured by ultra performance liquid chromatography (RP-UPLC) and particle count is measured by focused beam reflectance measurement (FBRM).

Additional key design features included short processing cycle time and a stable crystal slurry amenable to downstream processing. During development, it was observed that a reduction in temperature from 25° C. to 5° C. dramatically accelerated crystal formation, driving it to >85% conversion within 4 hours. A typical crystallization profile is shown in FIG. 2, with crystal conversion measured by off-line UPLC analysis and particle count monitored in situ using FBRM. Isopropanol levels in the crystallization and cake wash were investigated as a means to increase the rate of drying. The slurry was found to be stable at 2-8° C. in the presence of 10% isopropanol for at least 7 days, whereas in 25% isopropanol approximately 10% yield was lost to crystal dissolution after 3 days (data not shown).

The crystallization process reliably produces rhombohedral insulin lispro crystals with an average crystal size of greater than 40 μm. A representative photomicrograph obtained at 10× magnification is shown in FIG. 3. X-ray crystallography was performed to determine whether the structure was consistent with previously published structures for hexameric zinc insulin lispro. To ensure that the obtained structures were representative of the designed crystallization process, the process was not optimized for X-ray analysis. One process modification was made to enable the growth of large single crystals—it was observed that crystallization at 25° C. (without the 5° C. temperature reduction step) produced crystals that were morphologically comparable to the base process but larger in size and with lower overall crystal conversion. A representative single crystal X-ray diffraction image is shown in FIG. 4.

Figure 5:
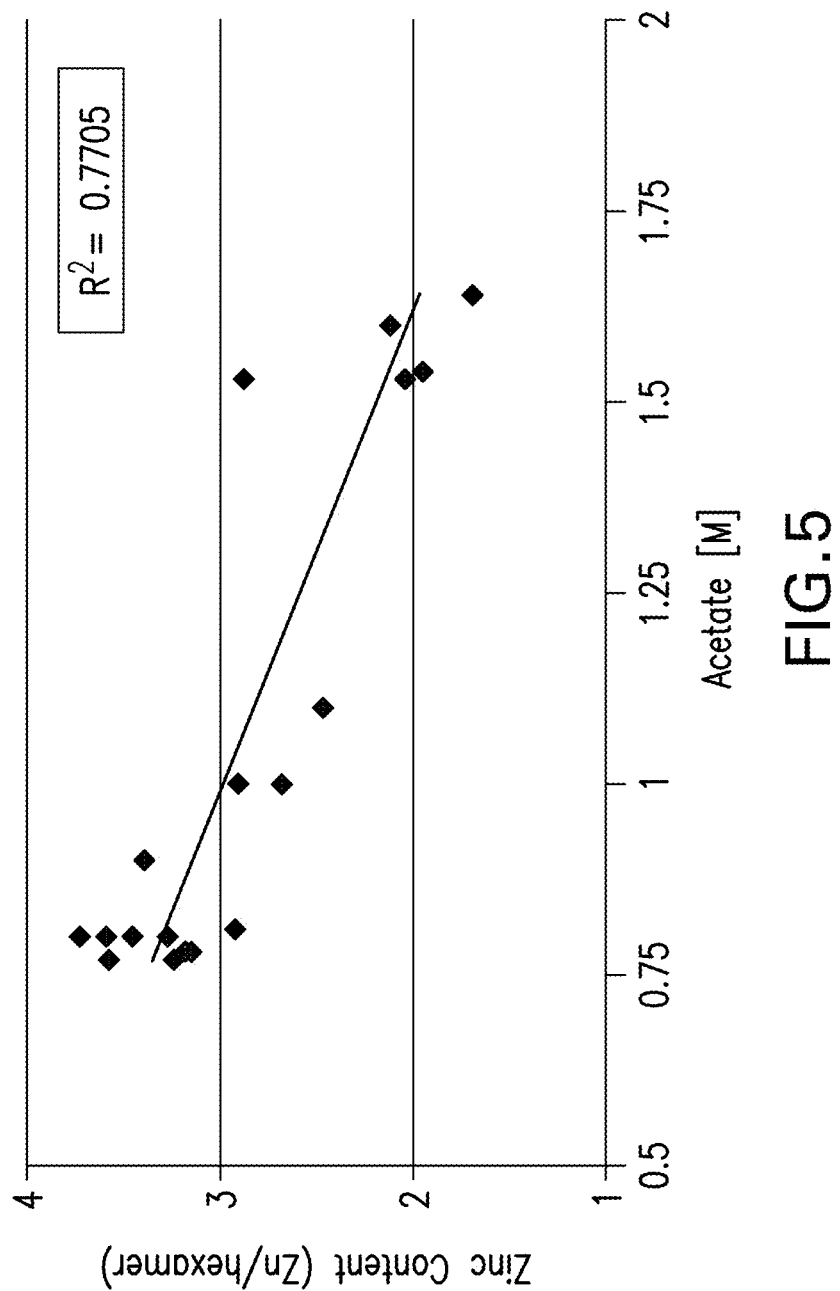
FIG. 5 shows impact of crystallization acetate level on zinc content of crystalline insulin lispro. In these experiments, crystallization acetate is isolated as a variable, with crystallization zinc and wash conditions held constant. In the range of 0.8 to 1.6 M acetate, increasing levels of organic acid/salt lead to lower levels of zinc in the range of approximately 3.3 to 2.1 zinc atoms per hexamer of insulin lispro.

Zinc control in the crystallization process was achieved through adjustment of the organic acid concentration. Depending on the conditions used, a minimum acetic acid concentration of approximately 0.5-1.0 M was required for crystallization to occur. Above the minimum threshold level, increasing amounts of acetic acid resulted in correspondingly lower zinc content in dried crystalline lispro (FIG. 5). On a molar basis, zinc content varied from approximately 3.3 zinc atoms per lispro hexamer when crystallized in 0.8 M acetic acid to approximately 2.1 zinc atoms per lispro hexamer when crystallized at 1.6 M acetic acid (Table 2).

TABLE 2

Impact of crystallization acetate level on zinc content of crystalline insulin lispro.

| Acetate Range [M] | Number of Runs (n) | Zinc Content (Zn/hexamer) |
|---|---|---|
| 0.77-0.81 | 9 | 3.3 ± 0.3 |
| 0.90-1.10 | 4 | 2.9 ± 0.4 |
| 1.53-1.64 | 5 | 2.1 ± 0.4 |

For these experiments, zinc concentration during crystallization was held constant at 0.40-0.45 mM. In addition, operating scale, equipment, and wash conditions did not impact the zinc content of dried DS in these studies. Ultimately, the lower acetic acid condition was selected for further development in conjunction with a filter drying process due to the zinc control afforded during filtration and the reduced overall acetic acid usage in the process.

Figure 6B:
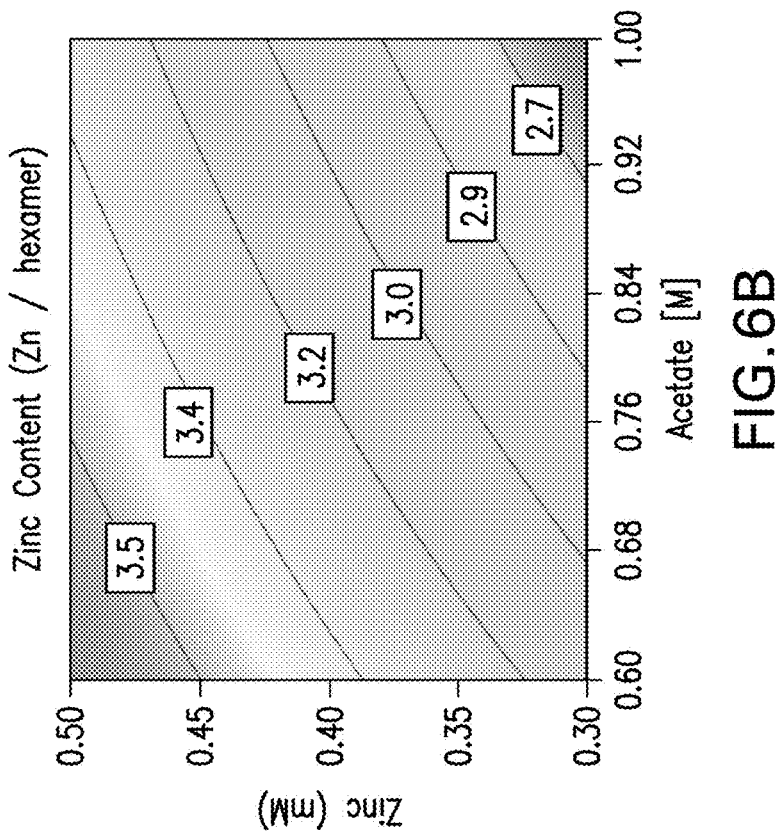
FIGS. 6A and 6B shows robustness of insulin lispro crystallization process. A five factor Design of Experiments study evaluated the impact of lispro concentration, acetate concentration, isopropanol concentration, zinc concentration, and agitation rate (tip speed) on zinc content of crystalline insulin lispro. Zinc content of dried crystalline insulin lispro was impacted by zinc and acetic acid levels in crystallization (FIG. 6A). Within the zinc and acetic acid ranges evaluated, final zinc content was found to vary within a range comparable to that previously observed during development (FIG. 6B). Zinc content was not affected by lispro concentration, isopropanol concentration, or agitation rate.
Figure 6A:
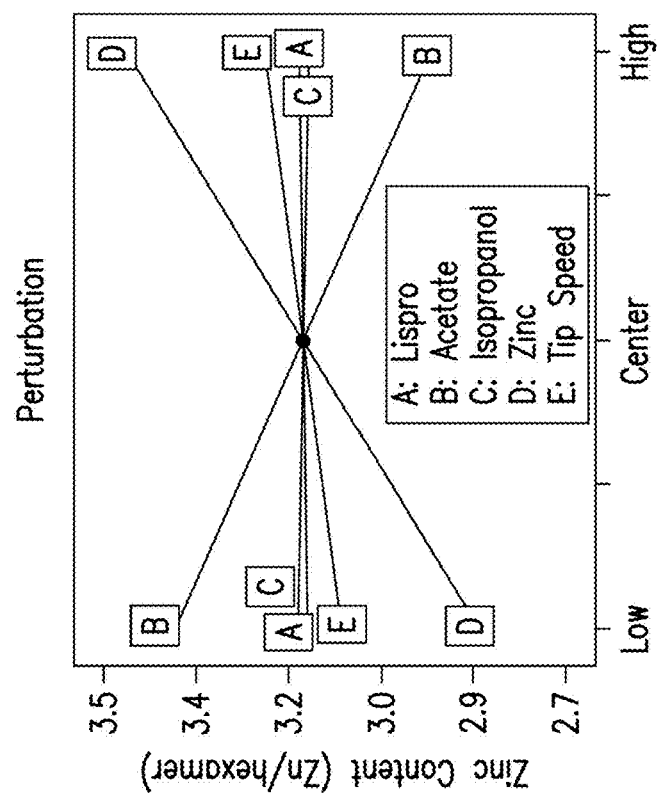

Process robustness around the center point condition was assessed through a half fraction factoral study. A five factor Design of Experiments study evaluated the impact of lispro concentration, acetate concentration, isopropanol concentration, zinc concentration, and agitation rate (tip speed) on zinc content of crystalline insulin lispro. Crystallization yield and insulin lispro quality were not impacted by any parameter within the ranges evaluated. However, zinc content of dried crystalline insulin lispro was impacted by zinc and acetic acid levels in crystallization (FIG. 6A). Within the zinc and acetic acid ranges evaluated, final zinc content was found to vary within a range comparable to that previously observed during development (FIG. 6B).

Filtration Process Development.

A filter drying process for harvesting the crystal slurry was incorporated into the process design to enable a cake wash step to serve as a second zinc control point. Development studies showed that the acetic acid concentration and pH of the cake wash were important in maintaining crystal integrity during washing. Below a minimum acetic acid threshold, insulin lispro crystal cakes were observed to convert to an unfilterable, amorphous state. This amorphous conversion was manifested during processing as dramatically reduced filtration flux and visible breakthrough of product across the filter screen.

The minimum acetic acid concentration required to maintain crystallinity varied according to the pH of the solution. When washing at a pH of approximately 7.5 (matching the crystallization pH), a minimum acetic acid concentration of 0.5 M was required. However, if the cake wash pH was reduced to the approximate isoelectric point of insulin lispro (pH 5.5), acetic acid could be reduced to 0.2 M without impacting crystallinity. The pH 7.5 wash condition did not affect lispro zinc content—in lab scale studies, dried insulin lispro contained 3.3±0.3 zinc atoms hexamer using base crystallization conditions without a cake wash (Table 2) and 3.2±0.5 zinc atoms per hexamer after washing at pH 7.5 (Table 3). In contrast, the pH 5.5 wash condition consistently reduced the zinc content to 2.5 zinc atoms per lispro hexamer with little variability (Table 3).

TABLE 3

Impact of cake wash buffer parameters on zinc content of crystalline insulin lispro.

| Wash Condition | pH 7.5 0.5M Acetate | pH 5.5 0.2M Acetate |
|---|---|---|
| Number of experiments | 6 | 5 |
| Zinc (Zn/hexamer) | 3.2 ± 0.5 | 2.5 ± 0.1 |

Across these experiments, comparable zinc content prior to washing was achieved through constant acetic acid (0.8-1.0 M) and zinc (0.40-0.45 m) concentrations during crystallization. Due to the consistent control of zinc demonstrated, the pH 5.5 wash condition was selected for scale-up.

Process Scale-Up

The integrated crystallization and filter drying process was demonstrated at pilot scale. Seven crystallizations were performed at an average scale of 40 g insulin lispro and yielded 87.1±5.2% (from crystallization to dried powder, adjusted for water content; Table 4). During scale up, it was demonstrated that the order of addition of crystallization diluent and lispro product feed could be reversed, with product being first added to the tank and other components being subsequently added and the titrated through the isoelectric point to achieve the target pH of 8.0. This change provided additional flexibility for process facility fit without impacting consistency or quality.

TABLE 4

Performance of optimized insulin lispro crystallization and filter drying process at pilot scale.

| Attribute | Result |
|---|---|
| Number of batches | 7 |
| Yield (%) | 87.1 ± 5.2 |
| Particle size (μm) | 57.8 ± 13.2 |
| Zinc content (wt %) | 0.44 ± 0.04 |
| Metacresol content (mg/g lispro) | 0.02 ± 0.01 |
| Loss on drying (%) | 7.1 ± 1.6 |

The dried crystalline material obtained at pilot scale was analyzed to determine particle size, the levels of residual zinc and meta-cresol, and overall loss on drying. Laser diffraction analysis showed an average particle size of 57.8 μm, consistent with the crystal sizes observed by light microscopy in crystal slurries. Zinc content and residual meta-cresol were tightly controlled. Loss on drying was somewhat more variable due to dependence on water content, which is determined by drying time. Zinc content and loss on drying were within the pharmacopeial limits specified in the USP and EP monographs for insulin lispro. In summary, pilot scale experience confirmed that the crystallization and filter drying process is scalable and reproducible.

Data processing yielded a complete dataset to 2.55 Å resolution with acceptable scaling and reduction statistics (see Table 5). The crystal form corresponded to the published structure of insulin lispro (PDB code 1LPH) with cell dimensions a=b=78.2 Å, c=38.1 Å and space group H3. Structure solution by molecular replacement, using a single insulin heterodimer derived from PDB code 1LPH (Ciszak et al. Op cit.) stripped of water and zinc atoms resulted in a model containing two insulin lispro heterodimers in the crystallographic asymmetric unit. The model was further improved using rigid-body refinement and a single cycle of positional and B-factor refinement. The resulting crystallographic model exhibited an $R_{free}$ value of 31%. There were two large peaks (at 12 and 13 times the rmsd of the electron density) in the difference Fourier map corresponding to the expected positions of the zinc ions chelated by residue His-B5. Inclusion of these two zinc atoms into the crystallographic model reduced the $R_{free}$ value to 28% and accounted for the observed difference density. This observation is consistent with identification of two ordered zinc sites per insulin hexamer. At the observed resolution and data quality, it was not possible to interpret the electron density in the vicinity of the expected phenolic stabilizer. With the crystal form identification, the interpretation of the two crystallographic zinc sites and examination of the expected location of the phenolic stabilizer, the structure was not refined to completion.

TABLE 5

Single crystal diffraction data collection and processing statistics

| | |
|---|---|
| Incident wavelength (Å) | 1.000 |
| Frame width (°, total sweep) | 0.25 (180) |
| Space Group | H 3 |
| Cell Dimensions (Å) | a = b = 78.2, c = 38.1 |
| Resolution (Å; outer shell) | 39-2.55 (2.56-2.55) |
| Rmerge (outer shell) | 0.041 (0.437) |
| <I/σI> (outer shell) | 18.6 (3.4) |
| Completeness (%, outer shell) | 99.8 (100) |
| Multiplicity (outer shell) | 5.1 (4.9) |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:
1. A method for preparing insulin lispro crystals comprising:
   (a) providing a solution comprising the insulin lispro, a water miscible organic solvent, and a crystal stabilizing agent, wherein the solution has a pH that is about 8.0; and
   (b) adding a zinc salt to the solution at a temperature of about 25° C. to provide a crystalizing solution, cooling the solution to about 5° C., and incubating the crystalizing solution for a time sufficient for the insulin lispro to produce the insulin lispro crystals.
2. The method in claim 1, wherein the solution comprises an organic acid or salt selected from the group consisting of acetic acid, acetate, citric acid, citrate, and glycine.
3. The method in claim 2, wherein the organic acid or salt comprises acetate.
4. The method in claim 1, wherein the solution comprises a base selected from the group consisting of potassium hydroxide, sodium hydroxide, and ammonium hydroxide.
5. The method in claim 4, wherein the base comprises ammonium hydroxide.
6. The method in claim 1, wherein the insulin lispro comprises a concentration in the range of 1.5 g/L of 2.5 g/L.
7. The method in claim 1, wherein the water miscible organic solvent comprises isopropanol.
8. The method in claim 1, wherein the crystal stabilizing agent comprises meta-cresol.
9. The method in claim 1, wherein the zinc salt comprises zinc chloride.
10. The method of claim 1, wherein the crystal stabilizing agent comprises meta-cresol and the solution further includes phenol at a concentration not more than 0.08 mM.
11. The method of claim 1, wherein the crystal stabilizing agent comprises meta-cresol and the solution does not include phenol.
12. The method in claim 1, wherein following the crystallization of the insulin lispro, a crystal slurry comprising the insulin lispro crystals is produced by (i) allowing the insulin lispro crystals in the crystalizing solution to settle in the crystalizing solution and the crystalizing solution decanted from the settled insulin lispro crystals or (ii) by centrifuging the crystallizing solution to remove the crystallizing solution from the insulin lispro crystals.
13. The method of claim 12, wherein the crystal slurry is applied to a filter apparatus to remove remaining crystalizing solution from the crystal slurry to produce a crystal cake bed and drying the crystal cake bed to provide the crystal insulin lispro.
14. The method of claim 12, wherein the crystal slurry is applied to a filter apparatus to remove remaining crystalizing solution from the crystal slurry to produce a crystal cake bed, washing the crystal cake bed with a cake wash solution comprising a water miscible organic solvent, a crystal stabilizing agent, and a zinc salt wherein the solution has a pH that of about 5.5, and drying the crystal cake bed to provide the crystal insulin lispro.
15. The method of claim 12, wherein the crystal slurry is applied to a centrifuge to remove remaining crystalizing solution from the crystal slurry, washing the crystals with a cake wash solution comprising a water miscible organic solvent, a crystal stabilizing agent, and a zinc salt wherein the solution has a pH that comprises about 4.5 to 8.5, and drying the crystals to provide the crystal insulin lispro.
16. A method for preparing insulin lispro crystals with 0.30% to 0.60% zinc content (dried basis), or about two to three zinc atoms per hexamer of insulin or insulin analog, comprising:
   (a) providing a solution comprising the insulin lispro, a water miscible organic solvent, and a crystal stabilizing agent, wherein the solution has a pH that is about 8.0;
   (b) adding zinc chloride to the solution at about 25° C. to provide a crystalizing solution, cooling the crystalizing solution to about 5° C., and incubating the crystalizing solution for a time sufficient produce insulin lispro crystals;
   (c) removing the crystalizing solution from the insulin lispro crystals to produce a crystal slurry;
   (d) applying the crystal slurry to a filter apparatus or centrifuge to remove remaining crystalizing solution from the decanted crystal slurry to produce a crystal cake bed;
   (e) adding a cake wash solution comprises a water miscible organic solvent, a crystal stabilizing agent, and zinc salt, wherein the solution has a pH that is about 5.0 to the decanted crystal slurry to provide a mixture and incubating the mixture for a time sufficient to remove unbound zinc from the insulin lispro, and
   (f) removing the cake wash solution from the mixture to provide the insulin or insulin analog crystals with 0.30% to 0.60% weight percent zinc content (dried basis), or approximately two to three zinc atoms per hexamer of insulin lispro.

17. A crystalline composition comprising insulin lispro, 0.30% to 0.60% zinc content (dried basis), or about two to three atoms of zinc per six molecules of the insulin or insulin analog, and meta-cresol wherein the insulin lispro crystals are cubic and have a 20-30 μm average crystal size or rhombohedral and have an average crystal size of greater than 40 μm.

* * * * *